United States Patent
Nagashio et al.

(10) Patent No.: US 8,328,355 B2
(45) Date of Patent: Dec. 11, 2012

(54) OPHTHALMIC DEVICE

(75) Inventors: Masanori Nagashio, Itabashi-ku (JP);
Kanichi Tokuda, Itabashi-ku (JP);
Taisaku Kogawa, Itabashi-ku (JP);
Hiroyuki Ootsuka, Itabashi-ku (JP)

(73) Assignee: Kabushiki Kaisha Topcon, Tokyo (JP)

( * ) Notice: Subject to any disclaimer, the term of this patent is extended or adjusted under 35 U.S.C. 154(b) by 91 days.

(21) Appl. No.: 12/864,145

(22) PCT Filed: Jan. 22, 2009

(86) PCT No.: PCT/JP2009/050945
§ 371 (c)(1),
(2), (4) Date: Jul. 22, 2010

(87) PCT Pub. No.: WO2009/093641
PCT Pub. Date: Jul. 30, 2009

(65) Prior Publication Data
US 2010/0296057 A1    Nov. 25, 2010

(30) Foreign Application Priority Data
Jan. 24, 2008    (JP) .................. 2008-013987

(51) Int. Cl.
*A61B 3/00*    (2006.01)
*A61B 3/14*    (2006.01)
(52) U.S. Cl. .................. 351/206; 351/200; 351/208
(58) Field of Classification Search .................. 351/200, 351/203, 205, 206, 208, 216, 221, 222
See application file for complete search history.

(56) References Cited

U.S. PATENT DOCUMENTS

| | | | |
|---|---|---|---|
| 5,548,354 A | 8/1996 | Kasahara et al. | |
| 5,572,266 A | 11/1996 | Ohtsuka | |
| 6,779,890 B2 * | 8/2004 | Matsumoto | 351/206 |
| 2009/0323023 A1 | 12/2009 | Kogawa et al. | |

FOREIGN PATENT DOCUMENTS

| | | |
|---|---|---|
| EP | 0 628 281 | 6/1994 |
| EP | 1 864 609 | 12/2007 |

(Continued)

OTHER PUBLICATIONS

International Search Report issued Feb. 17, 2009 in International (PCT) Application No. PCT/JP2009/050945.

*Primary Examiner* — Thomas K Pham
*Assistant Examiner* — Brandi Thomas
(74) *Attorney, Agent, or Firm* — Wenderoth, Lind & Ponack, L.L.P.

(57) ABSTRACT

An ophthalmic device is provided with a photographing optical system that photographs an eye fundus; an illumination optical system that illuminate the eye fundus; a split target projection optical system that projects a split target for focusing the photographing optical system on the eye fundus; an alignment target projection optical system that projects an alignment target (AL) for aligning the photographing optical system with an examining eye; an observation optical system that displays optical images of the eye fundus; and a pseudo-target display processing unit that takes an observation video signal output by the observation optical system in, detects at least one of positions of the split target and the alignment target in the observation video signal, and displays a pseudo-target on the monitor in accordance with the detected position.

8 Claims, 13 Drawing Sheets

FOREIGN PATENT DOCUMENTS

| | | |
|---|---|---|
| JP | 7-75624 | 3/1995 |
| JP | 7-227380 | 8/1995 |
| JP | 9-253053 | 9/1997 |
| JP | 3379592 | 12/2002 |
| JP | 2003-290145 | 10/2003 |
| JP | 2006-280477 | 10/2006 |
| WO | 2006/106977 | 10/2006 |

* cited by examiner

ALIGNMENT LUMINESCENT SPOTS DETECTION AREA

ALIGNMENT LUMINESCENT SPOTS DETECTION METHOD

OPHTHALMIC DEVICE

CROSS-REFERENCE TO RELATED APPLICATION

The present application is based on and claims priority from Japanese Patent Application No. 2008-013987, filed on Jan. 24, 2008, the disclosure of which is hereby incorporated by reference in its entirety.

BACKGROUND OF THE INVENTION

The invention relates to an ophthalmic device like a fundus camera.
I. Technical Field
II. Description of the Related Art

BACKGROUND ART

A conventional fundus camera has an alignment target for adjusting a distance between an objective lens of a photographing optical system and an eye to be examined (hereinafter referred to as a working distance) and aligning the objective lens with the eye to be examined, and a split target for focusing the photographing optical system on the eye to be examined. An optical image of the alignment target and an optical image of the split target, which are received by an observation camera, are displayed on a monitor.

An examiner performs an alignment adjusting operation for matching the centers of two separate alignment targets, through operation of a joy stick, while looking at the alignment targets displayed on a monitor. The examiner also performs a focusing operation for aligning upper and lower split targets by turning an adjusting knob while looking at the split targets.

However, when performing an alignment adjusting operation and a focusing operation, an examiner needs to check the states or the alignment targets and split targets while looking at an eye fundus image, which imposes a heavy burden on the examiner.

A fundus camera performing automatic focusing to reduce the burden on the examiner during the focusing operation has been known (see Japanese Patent Application Publication No. Hei7-227380, for example). In addition, a fundus camera performing automatic alignment to reduce the burden on the examiner during the alignment adjusting operation has also been known (see Japanese Patent No. 3379592, for example).
Patent Document 1: Japanese Patent Application Publication No. Hei7-227380
Patent Document 2: Japanese Patent No. 3379592

SUMMARY OF THE INVENTION

In the case of a conventional fundus camera, however, an examiner performs a focusing operation using optical images of split targets which are photographed by an observation camera and displayed on a monitor. This causes a problem that even a skilled examiner has difficulty in performing the focusing operation when optical images of the split targets are out of focus and difficult to confirm visually or when only one of upper and lower split targets is visible. In particular, when an eye to be examined has a small pupil, and when one split target is blocked by the pupil of the eye to be examined, for example, the focusing operation is difficult. This is because an examiner should perform the focusing operation in such a way to align the upper and lower split targets with each other by performing an operation of alternately projecting the upper and lower split targets on the eye fundus of the eye to be examined by slightly moving a pedestal from side to side.

In addition, the fundus camera described in Japanese Patent Application Publication No. Hei7-227380 which performs the automatic focusing operation by using optical images of split targets. Thus, the fundus camera has a problem of being incapable of completing the automatic focusing operation when the optical images of the split targets are out of focus or when only one of the upper and lower split targets can be detected.

In addition, the fundus camera described in Japanese Patent No. 3379592 performs the automatic alignment operation by using an optical image of an alignment target. Thus, the fundus camera has a problem of being incapable of completing the adjustment of the working distance or the alignment by the automatic alignment operation when the optical image of the alignment target is out of focus or when only one of two alignment targets can be detected. Additionally, the fundus camera described in Japanese Patent No. 3379592 should have a mechanism for causing each of the two alignment targets to flash when the two alignment targets are separated due to an inappropriate working distance, which leads to complication of a device or cost increase.

The invention aims to provide an ophthalmic device in which allows an alignment adjusting operation and a focusing operation to be easily carried out by a manual operation and the alignment adjusting operation or the focusing operation to be surely accomplished at an automatic operation regardless of the display states of targets in optical images used for carrying out the alignment adjusting operation and the focusing operation.

According to one aspect of the invention, an ophthalmic device characterized by comprising: a photographing optical system that photographs an eye fundus; an illumination optical system that illuminates the eye fundus; a split target projection optical system that projects a split target for focusing the photographing optical system on the eye fundus; an alignment target projection optical system that projects an alignment target for aligning the photographing optical system with an examining eye; an observation optical system that displays optical images of the eye fundus; and a pseudo target display processing unit that takes an observation video signal output by the observation optical system in, detects at least one of positions of the split target and the alignment target in the observation video signal, and displays a pseudo target on the monitor in accordance with the detected position.

In an ophthalmic device of the invention, not only optical image targets but also pseudo targets are displayed on an observation monitor. This enables an alignment adjusting operation and a focusing operation to be performed at manual operation by using the pseudo targets with operating procedure similar to conventional operating procedure. In addition, the displayed pseudo target is easier to recognize than the optical image target and the visibility of the target is improved. Therefore, an operation of matching two targets is easier than when the optical image targets are used. Furthermore, at automatic operation, since the pseudo target which is easier to recognize than target optical image is displayed on the monitor, performance of position detection of the pseudo target is better than performance of position detection of the optical image target. Therefore, the ophthalmic device of the invention is capable of aligning the eye to be examined with a non-mydriasis fundus camera or focusing the non-mydriasis fundus camera on the eye to be examined in prompt and reliable manner.

DETAILED DESCRIPTION OF THE INVENTION

Figure 1:
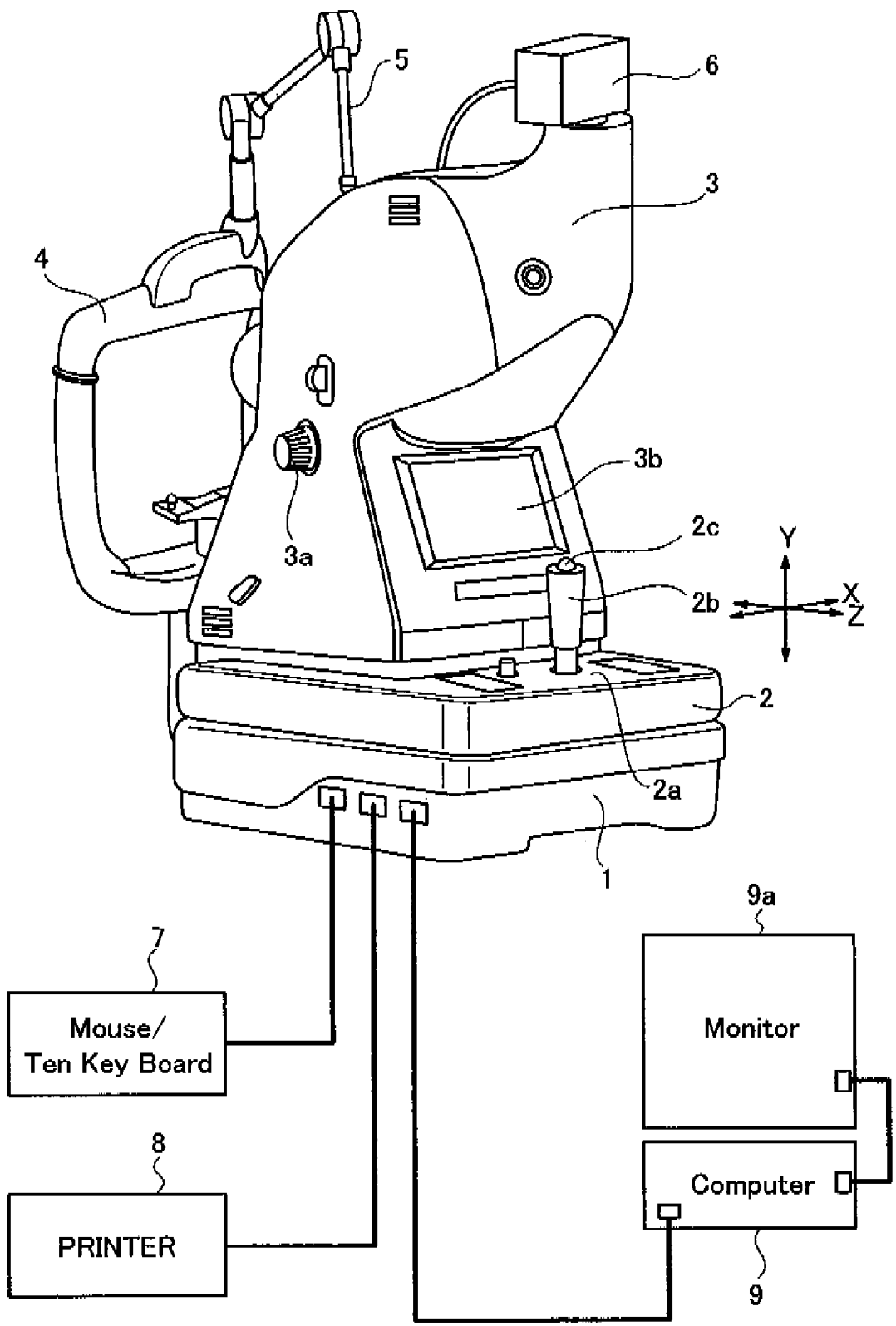
FIG. 1 shows an external appearance view of a non-mydriasis fundus camera (one example of the opthalmological imaging apparatus) of a first example according to the invention.

Hereafter, the best mode embodiment which realizes the opthalmological imaging apparatus of the invention will be explained based upon a working example 1 shown in the Drawings.

Working Example 1

Firstly, the constituent structural feature of working examples will be explained. FIG. 1 is an external appearance view of a non-mydriasis fundus camera (one example of the opthalmological imaging apparatus) of a working example 1 according to the invention. Here, the "non-mydriasis fundus camera" refers to a fundus camera which observes an eye ground and takes a photograph of the eye ground by emitting a flash light after carrying out mydriasis to some extent in a darkroom without using a mydriatic. This non-mydriasis fundus camera has advantage of not causing eyesight inconvenience after an inspection while the inspection is simple, and is used in not only ophthalmology but internal medicine and a medical examination. The non-mydriasis fundus camera is disadvantageous in that the non-mydriasis fundus camera can photograph only a center portion of the retina since mydriasis is insufficient compared with the case in which a mydriatic is used. For this reason, in the case of a small pupil due to diabetic retinopathy and so on, the inspection is difficult.

The non-mydriasis fundus camera of the working example 1 includes a device base 1, a pedestal part 2, a device main body 3, a chin rest 4, an external fixed target 5, an imaging CCD camera 6 (camera), a mouth and a ten key board 7, a printer 8, a computer 9, and a display 9a, as shown in FIG. 1.

The device base 1 is horizontally installed on a device table (not shown) and provided with a power source plug and a plurality of connection terminals. This device base 1 contains a power source section, a jaw receptacle PCB, a relay PCB, etc. Further, PCT is an abbreviation for Printed Circuit Board and is a printed circuit board on which IC etc. are mounted.

The pedestal part 2 is provided to be movable relative to the device base 1 in a right/left direction, in a forward/backward direction, and in a vertical direction. An operation panel 2a, a joy stick 2b, a photographing switch 2c, etc. are provided at a position on the examiner's side of this pedestal part 2.

The device main body 3 is integrally provided on the upper part of the pedestal part 2. A focusing handle 3a is provided at a position on the lateral side of the main body 3. A display 3b (6.5 type color liquid crystal display (LCD), for example), which is a constituent part of a monitor 31 (see FIG. 5) is provided at a position on the examiner's side of the device main body 3. Further, LCD is an abbreviation for Liquid Crystal Display.

The chin rest 4 is provided so that its position relative to the device base 1 can be adjusted in a vertical direction. The chin rest 4 comes into touch with an examinee's chin and forehead and thereby fixes the position of an eye to be examined. The chin rest 4 is provided with an external fixed target 5 for fixing an examinee's line of sight.

The imaging CCD camera 6 is installed on the upper part of the device main body 3, and takes a photograph of an eye ground with a flare of flashlight by means of an auto shoot function that the non-mydriasis fundus camera of the working example 1 has. A commercially available digital camera of APS size is used as this imaging CCD camera 6. The imaging CCD camera 6 is powered by the power source section contained in the device base 1.

The mouse and the ten key board 7, the printer 8, and the computer 9 are connected with connection terminals provided on the device base 1 through cables, respectively. In addition, a display 9a, which enables observation of an eye ground on a screen, is connected to the computer 9.

Figure 2:
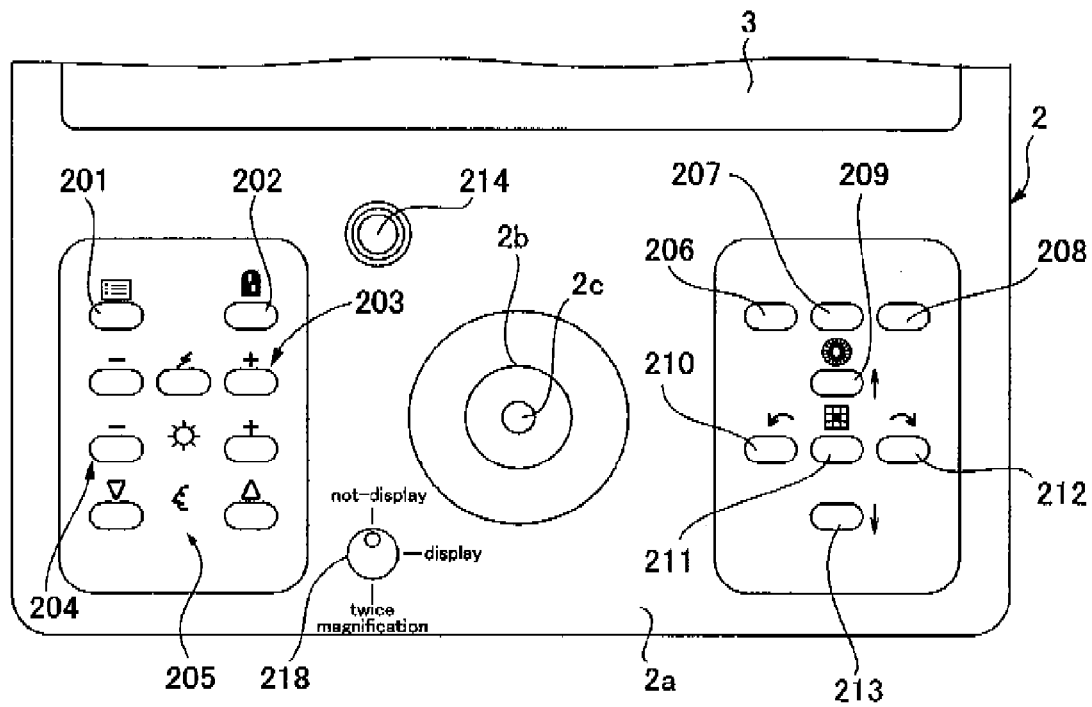
FIG. 2 shows a plan view of an operation panel provided on a pedestal part of the non-mydriasis fundus camera of the first example according to the invention.

FIG. 2 is a plan view of the operation panel 2a provided on the pedestal part 2 of the non-mydriasis fundus camera of the working example 1. The following explains switches, etc. provided on the operation panel 2a.

As shown in FIG. 2, the operation panel 2a provided on the pedestal part 2 includes the joy stick 2b, the photographing switch 2c, a menu switch 201, a split switch 202, an imaging light amount correction switch 203, an observation light amount correction switch 204, a chin rest position adjustment switch 205, an ID input switch 206, an image deletion switch 207, an image replay switch 208, a small pupil switch 209, visual fixation switching switches 210, 211, 212, an automatic ON/OFF switch 213, a magnification change switch 214, and a pseudo target display setting part 218.

The joy stick 2b is operation means for moving the pedestal part 2 and the device main body 3 relative to the device base 1 in a right/left direction (X direction), in a vertical direction (Y direct ion), and in a forward/backward direction (Z direction) when an alignment operation is manually carried out. When moving the pedestal part 2 and the device main body 3 in the right/left direction and in the forward/backward direction, an examiner holds the joy stick 2b and tilts the joy stick 2b in the right/left or forward/backward direction in which to move. At this time, a pedestal front/back detection switch 215 and a pedestal right/left detection switch 216 turn ON (see FIG. 5). In addition, when moving the pedestal part 2 and the device main body 3 in the vertical direction, an examiner turns an operation ring set on the upper part of the joy stick 2b clockwise (the pedestal part 2 and the device main body 3 move upward) or turns the operation ring anticlockwise (the pedestal part 2 and the device main body 3 moves downward).

The photographing switch 2c is an eye ground photographing shutter switch which is provided on the upper end of the joy stick 2b. An eye ground is photographed by an examiner's pressing down the photographing switch 2c. In addition to the photographing function, the photographing switch 2c also makes release from a review or power-saving mode.

The menu switch 201 turns ON/OFF a menu display on the monitor 31.

The split switch 202 switches ON/OFF of split targets or switches from the split targets to the fixed target. This change of the targets is carried out in the item "SPLIT SWITCH" in an initial setting menu of the non-mydriasis fundus camera of the working example 1.

The imaging light amount correction switch 203 corrects an imaging light amount. Starting from the left, FIG. 2 shows an imaging light amount minus correction switch, an imaging light amount reset switch, and an imaging light amount plus switch.

The observation light amount correction switch 204 corrects an observation light amount. Starting from the left, FIG. 2 shows an observation light amount minus correction switch and an observation light amount plus correction switch.

The chin rest position adjustment switch 205 adjusts a vertical position of the chin rest 4. Starting from the left, FIG. 2 shows a chin rest lowering switch and a chin rest raising switch.

The ID input switch 206 is a switch for displaying an ID input screen on the display screen of the monitor 31.

The image deletion switch 207 is a switch to be turned ON when an examiner deletes a reviewed photographed image.

When the image replay switch 208 is turned ON, an image imaged by the imaging CCD camera 6 is replayed and displayed on the monitor 31. While the image replay switch 208 is ON, the previous image is replayed every time the visual fixation switching switch 210 is turned ON, and the next image is replayed every time the visual fixation switching switch 212 is turned ON. When the image replay switch is turned OFF, the monitor 31 returns to the observation screen.

When the small pupil switch 209 is turned ON or OFF, a small pupil aperture AP is inserted into or removed from an illumination optical system. The small pupil switch 209 independently functions even when the auto ON/OFF switch 213 (to be described later) is in ON state. When the small pupil switch 209 is in ON state, a double circle is displayed on the screen of the monitor 31. When a photographing mode is set to a digital magnification change linked mode and the small pupil switch is turned ON (the small pupil aperture is inserted into the illumination optical system), data is saved with the imaging angle of view of 30°. In addition, if the image is printed in this state, the image is printed with the imaging angle of view of 30°. If the photographing mode is set to a digital magnification change unlinked mode, digital magnification change does not take place and the imaging angle of view remains at 45° even when the small pupil switch 209 is turned ON (the small pupil, aperture AP is inserted into the illumination optical system). This small pupil switch 209 also serves as a switch for moving up a selection cursor while a menu screen or an ID input screen is displayed on the monitor 31.

The visual fixation switching switch 210 switches an internal fixed target to a previous flashing (lighted-on) position from a current flashing (lighted-on) position of the internal fixed target. This visual fixation switching switch 210 also serves as a switch for moving a selection Cursor to the left while the menu screen or the ID input screen is displayed on the monitor 31.

The visual fixation switching switch 211 switches the internal fixed target to an initial flashing (lighted-on) position from the current flashing (lighted-on) position of the internal fixed target. This visual fixation switching switch 211 also serves as a print switch and an enter switch. When the visual fixation switching switch 211 works as the print switch, an image displayed on the monitor 31 is printed out by turning the visual fixation switching switch 2110N. Either when an automatic print function is set in menu setting or when a print execution display appears on the observation screen, printing is stopped when the visual fixation switching switch 211 is turned ON. When the visual fixation switching switch 211 works as the enter switch, a selected item or a character is determined on the menu screen or the ID input screen by turning the visual fixation switching switch 211 ON.

The visual fixation switching switch 212 switches the internal fixed target to the next flashing (lighted-on) position to the current flashing (lighted-on) position of the internal fixed target. This visual fixation switching switch 212 also works as a switch for moving the selection cursor to the right when the menu screen or the ID input screen is displayed on the monitor 31.

The automatic ON/OFF switch 213 turns ON/OFF an automatic shoot function, an autofocus function, or an automatic small pupil function. Here, each function is selected on the menu screen. This automatic ON/OFF switch 213 also serves as a switch for moving down the selection cursor when the menu screen or the input screen is displayed on the monitor 31.

The magnification change switch 214 is a switch for setting an imaging angle of view to 30° or 45° in order to takes a photograph of an eye ground with the magnification changed to twice.

The pseudo target display setting part 218 is a switch for switching a display state of pseudo split luminescent lines SL3 to be displayed on the monitor 31, that is, a state in which the pseudo split luminescent lines SL are not displayed on the monitor, a state in which the pseudo split luminescent lines SLV size of which is same as an optical image of the split luminescent lines SL is superimposed and displayed on the monitor 31, and a state in which the pseudo split luminescent lines SLV size of which is double of an optical image of the split luminescent lines SL.

Figure 3:
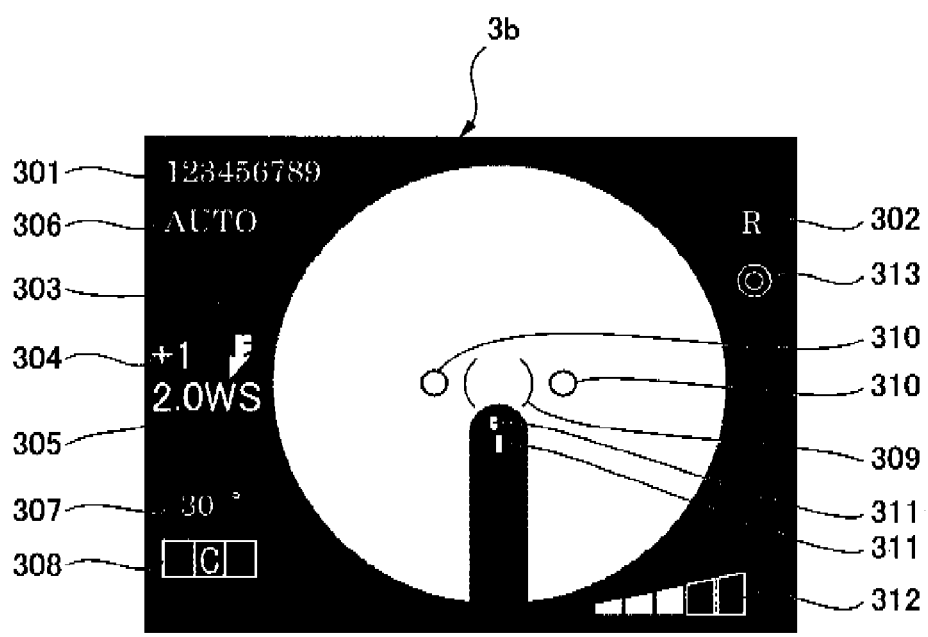
FIG. 3 shows a view illustrative of an image example of each of displaying items displayed an a monitor 31 provided on a device main body 3 of the non-mydriasis fundus camera of the first example according to the invention.

FIG. 3 is an image view of a display screen to be displayed on the monitor 31 set on the main device body 3 of the non-mydriasis fundus camera of the working example 1. Respective displaying items in the display screen will be explained hereinafter.

In the case of the non-mydriasis fundus camera of the working example 1, as shown in FIG. 3, information of the device main body 3 and information of the imaging CCD camera 6 are displayed on the monitor 31. When an eye ground is observed, when an photographed image is reviewed, when a photographed image is replayed, and when a menu screen is displayed, displaying items include a patient ID display 301, a display of an eye to be photographed 302, a xenon charging display 303, an imaging light amount correction display 304, an imaging light amount level display 305, an AUTO display 306, a photographing angle of view display 307, a visual fixation position display 308, a ( ) scale 309, alignment luminescent spots AL (310, 310) (alignment targets), split luminescent lines SL (311, 311) (split targets), an observation light amount level display 312, and a small pupil aperture display 313. In addition, the split luminescent lines (311, 311) also include pseudo split luminescent lines SLV (311V, 311V).

The patient 10 display 301 displays an ID of a patient whose eye ground image is photographed. The display of an eye to be photographed 302 displays an eye (R, L) whose fundus is photographed. The xenon charging display 303 shows charging condition of a power source for light emission of a xenon lamp (to be displayed), flashes during charging, and turns on when charging ends. The imaging light amount correction display 304 displays a corrected amount (+4 to −4) of imaging light amount on a panel switch 217 (see FIG. 5). The imaging light amount level display 305 displays an imaging light amount (0.8 ws to 45 ws).

The AUTO display 306 appears when any of automatic shooting function, autofocus function, or automatic small pupil switching function is ON. The view of angle display 307 displays a view of angle to be photographed. If the digital magnification change is set to a small pupil aperture linkage mode, it displays 30° when the small pupil aperture is inserted into the illumination optical system. The visual fixation position display 308 displays a visual fixation position by flashing a selected visual fixation position.

The ( ) scale 309 appears as a position where alignment luminescent spots AL match. The alignment luminescent spots (310, 310) are displayed as a target for aligning a working distance. The split luminescent lines SL (311, 311) are displayed as a target for aligning a diopter scale of an examinee. The observation light amount level display 312 displays the observation light amount level in 5 stages. The small pupil aperture display 313 displays a double circle when the small pupil aperture is inserted into the illumination optical system.

Figure 4:
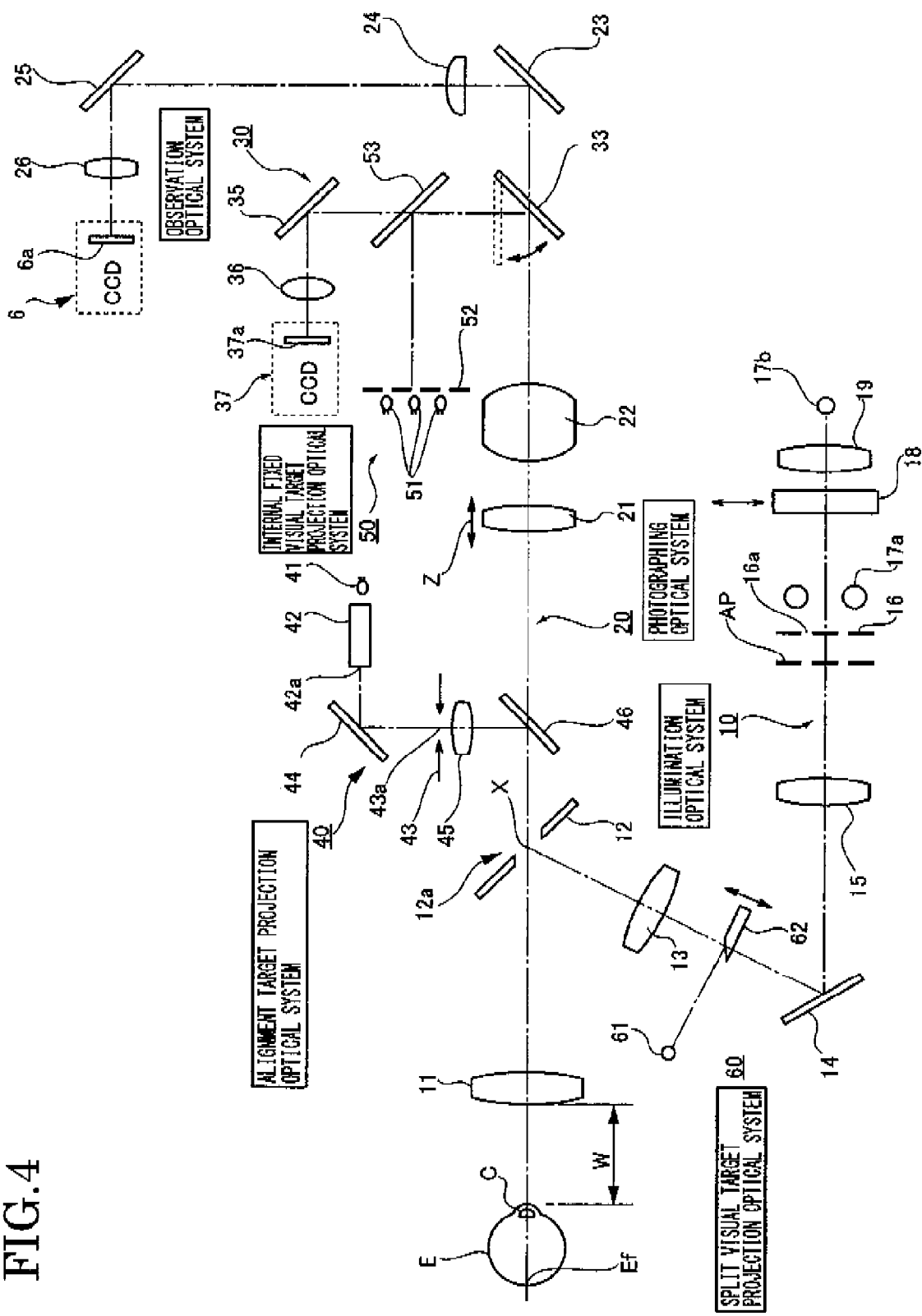
FIG. 4 shows a view of an optical system built-in the device main body 3 of the non-mydriasis fundus camera of the first example according to the invention.

FIG. 4 is a view of an optical system built-in the device main body 3 of the non-mydriasis fundus camera of the working example 1. A layout configuration of the optical system of the non-mydriasis fundus camera will be described hereinafter.

As shown in FIG. 4, inside of the device main body are provided the illumination optical system 10 for illuminating an eye fundus Ef of an eye to be examined E, a photographing optical system 20 for photographing an eye fundus Ef, an observation optical system 30 for observing an eye fundus Ef, an alignment target projector system 40 for aligning the device main body 3 with respect to the eye to be examined E, an internal fixed target projector system 50 for projecting a fixed target on the eye fundus Ef for visual fixation of the eye to be examined E, and a split target projector system 60 for focusing the optical system on the eye fundus Ef.

The illumination optical system 10 is an illumination optical system which illuminates an eye fundus Ef with infrared light when the eye fundus Ef of an eye to be examined E is observed, and which illuminates the eye fundus Ef with visible light when the eye fundus Ef of the eye to be examined E is photographed. This illumination optical system 10 has an objective lens 11, a perforated mirror 12, a relay lens 13, a reflecting mirror 14, a relay lens 15, a ring aperture plate 16 having a ring aperture 16a which is kept in a conjugate relation with a pupil of an eye to be examined E, a xenon lamp 17a as a photographing light source of the eye fundus Ef, an infrared filter 18, a condenser lens 19, and a halogen lamp 17b as an observation light source of the eye fundus Ef. The perforated mirror 12 is arranged at a position in a conjugate relation with the cornea C of the eye to be examined E when the objective lens 11 and the eye to be examined E are positioned at appropriate distance (working distance) W.

The photographing optical system 20 is an optical system for photographing, as a still image, the eye fundus Ef illuminated by the illumination optical system 10. This photographing optical system 20 includes the objective lens 11, the perforated mirror 12, a focusing lens 21, an imaging lens 22, a reflecting mirror 23, a field lens 24, a reflecting mirror 25, a relay lens 26, and a CCD 6a of the imaging CCD camera 6.

The observation optical system 30 is an optical system for observing the eye fundus Ef illuminated by the illumination optical system 10, and is configured by branching halfway on an optical path of the photographing optical system 20 by a quick return mirror 33. The observation optical system 30 includes a reflecting mirror 35, a relay lens 36, and a CCD 37a of an observation CCD camera 37.

The alignment target projector system 40 is designed to project an alignment luminescent spot AL toward an eye to be examined E. The alignment target projector system 40 includes a LED 41 as a light source for an alignment target, a light guide 42 for guiding light of the LED 41, a reflecting mirror 44 for reflecting light from the light guide 42 and guiding it to a two-aperture diaphragm 43, a relay lens 45, a half mirror for branching 46 located on the photographing optical system 20, the perforated mirror 12, and the objective lens 11. The two-aperture diaphragm 43 divides an alignment beam into two alignment luminescent spots AL (310, 310) and projects them on an eye to be examined E. That is to say, the alignment beam emitted from an exit end 42a of the light guide 42 is reflected by the reflecting mirror 44 and guided to the two-aperture diaphragm 43. The alignment beam which passes through aperture parts 43a, 43a of the two-aperture diaphragm 43 is guided to the relay lens 45. The alignment beam which passes through the relay lens 45 is reflected by a half mirror 46 toward the perforated mirror 12. The relay lens 45 once forms an intermediate image of the alignment beam, which is emitted from the exit end 42a of the light guide 42, at a center position X of the aperture part 12a of the perforated mirror 12. A pair of the alignment luminescent spots 310, 310 which form the alignment target imaged at the center position X of the aperture 12a is guided to a cornea or C of an eye to be examined E by way of the objective lens 11.

The internal fixed target projector system 50 is an optical system which projects an internal fixed target for guiding a center portion of an eye to be examined E and a periphery thereof onto an optical axis of the photographing optical system 20, and is arranged by being branched halfway from an optical path of the observation optical system 30 by a dichroic mirror 53 having the characteristic that it transmits infrared light and reflects visible light. The internal fixed target projector system 50 includes a LED 51 as a light source for an internal target, a mask plate 52, and the dichroic mirror 53. The LED 51 is configured to have 3 LEDs arranged in the center and 8 LEDs arranged equally spaced on the circumference centering on the 3 LEDs.

The split target projector system 60 is a projector system of split luminescent lines SL, and includes a LED 61 as a light source for a split target and a reflecting rod 62 provided in an optical path of the illumination optical system 10 and reflecting light from the ZED 61. The reflecting rod 62 is detachably inserted at a position which is optically conjugated with the eye fundus Ef of an eye to be examined E (for a detailed configuration thereof, refer to Japanese Patent No. 3696949, for example). The split target projector system 60 is designed to move to an optical axis of the illumination optical system 10, in conjunction with movement of the observation optical system 30 and the photographing optical system 20 toward a Z direction of the focusing lens 21 and to, so that the reflecting mirror of the reflecting rod 62 is always in a optically conjugate relation with the eye fundus Ef. If the reflecting mirror of the reflecting rod 62 is not in the conjugate relation with the eye fundus Ef, the split luminescent lines SL look like two separate lines to the right and left directions (311, 311), as shown in FIG. 3. Focusing of the eye fundus Ef can be performed by aligning these split luminescent lines SL (311, 311) that look like two separate lines to the right and left directions.

Figure 5:
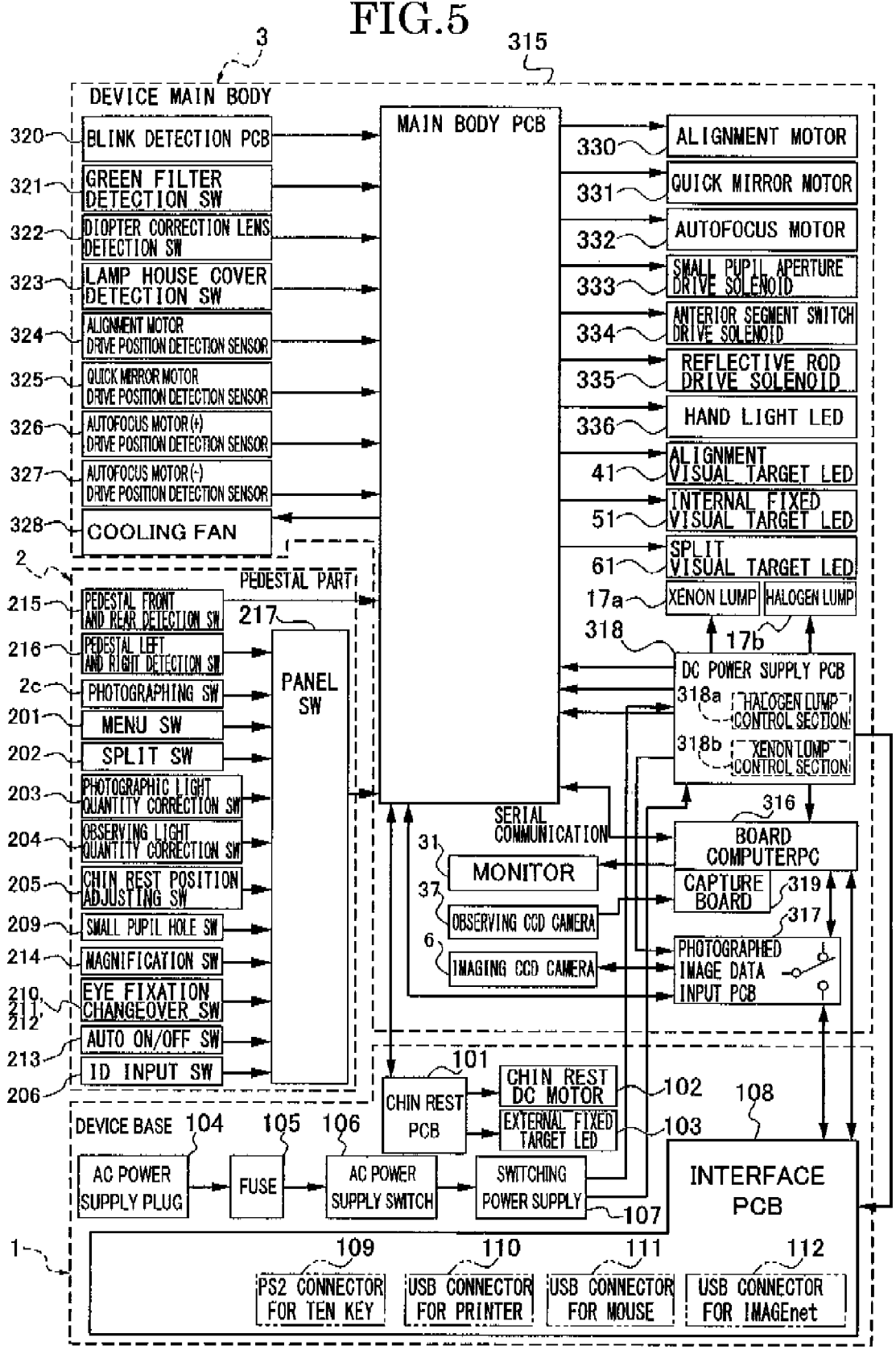
FIG. 5 shows an electric block diagram of a control system built-in a device base 1, the pedestal part 2 and the device main body 3 of the non-mydriasis fundus camera of the first example according to the invention.

FIG. 5 is an electric block diagram showing a control system contained in a device base 1, a pedestal part 2, and a device main body 3 of the non-mydriasis fundus camera of the working example 1. A configuration of the control system of the non-mydriasis fundus camera will be described hereinafter.

As shown in FIG. 5, the device base 1 includes a chin rest PCB 101, a chin rest DC motor 102, a LED 103 as a light source for an external fixed target, an alternating-current supply plug 104, a fuse 105, an alternating-current supply switch 106, a switched-mode power supply 107, and an interface PCB 108. The interface PCB 108 includes a PS2 connector 109 for ten keys, a USE, connector 110 for a printer, a USB connector 111 for a mouse, and an SB connector 112 for IMAGEnet of TOPCON Corp.

The pedestal part 2 is provided with a photographing switch 2c, a menu switch 201, a split switch 202, an imaging light amount correction switch 203, an observation light amount correction switch 204, a chin rest position detection switch 205, an ID input switch 206, a small pupil switch 209, visual fixation switching switches 210, 211, 212, an automatic ON/OFF switch 213, a magnification change switch 214, a pedestal forward/backward detection switch 215, a pedestal right/left detection switch 216, and a power switch 217, as shown in FIG. 5.

The device main body 3 is provided with an imaging CCD camera 6, a xenon lamp 17a, a halogen lamp 17b, a monitor 31, an imaging CCD camera 37, a main body PCB 315, a board computer 316, a data communications PCB 317, a DC power supply PCB 318, and a capture board 319. In addition, the DC power supply PCB 318 includes a halogen lamp control section 318a and a xenon lamp control section 318b, as shown in FIG. 5.

The device main body 3 is provided with, as information input means to the main body PCB 315, a blink detection PCB 320, a green filter detection switch 321, a diopter scale correction lens detection switch 322, a lamp house cover detection switch 323, an alignment motor driving position detection sensor 324, a quick mirror motor drive position detecting sensor 325, an autofocus motor (+) drive position detecting sensor 326, and an autofocus motor (−) drive position detecting sensor 327, as shown in FIG. 5.

In addition, the device main body 3 is provided with, as control command output means from the main body PCB 315, a cooling fan 328, an alignment motor 330 (alignment actuator), a quick mirror motor 331, an autofocus motor 332 (autofocus actuator), a small pupil aperture driving solenoid 333, an anterior eye segment switch driving solenoid 334, a reflecting rod driving solenoid 335, a LED 336 as a light source for illuminating hands, a LED 41 as a light source for alignment target, a LED 51 as a light source for an internal fixed target, and a LED 61 as a light source for a split target.

The main body PCB 315 exchanges data with the board computer 316 through serial communications. In addition, the main body PCB 315 exchanges data with a photographing data input PCB 317 through two-way communications. In addition, the board computer 316 exchanges data with each of the photographing data input PCB 317, the board computer 316 exchanges data with the interface PCB 108, and the photographing data input PC 317 exchanges data with the interface PCB through two-way communications.

The main body 315 serves the following functions:

(1) Various Types of Detection by the Sensors and Switches

On the basis of the respective sensors and switches, the main body PC 315 carries out blink detection, green filter detection, diopter scale correction lens detection, lamp house cover detection, alignment motor driving position detection, quick mirror drive position detection, and autofocus motor drive detection.

(2) Driving a Motor

The main body PCB 315 performs driving control of the alignment motor, the quick motor, and the autofocus motor.

(3) Driving a Driving Solenoid

The main body PCB 315 performs driving control of the small pupil aperture driving solenoid 333, the anterior eye segment switch driving solenoid 334, and the reflecting rod driving solenoid 335.

(4) Lighting Up a LED

The main body PCB 315 controls lighting up and flashing of the LED 336 as the light source for illuminating hands, the LED 41 as the light source for the alignment target, the LED 51 as the light source for the internal fixed target, and the LED 61 as the light source for the split target.

(5) Reading a Switch Signal

The main body 315 reads various switch signals from the pedestal part 2.

The board computer 316 (single board computer) serves the following functions:

(1) Direct Print Function

The board computer 316 performs direct print which directly transfers an image photographed by the imaging CCD camera 6 to the printer 8. Although a picto-bridge function is incorporated in the main body of the imaging CCD camera 6, an examiner should operate the main body of the imaging CCD camera 6 when printing, which thus complicates the operating procedure. Thus, operation is simplified by including a print-out function in a series of photographing operations.

(2) Autofocus Function

The board computer 316 analyzes a state of the split luminescent lines SL (311, 311) on a video signal to be obtained from the CCD 37a of the observation CCD camera 37, and performs an autofocus operation of the observation CCD camera 37. Analyzing a video signal on the board computer 316 enables an autofocus operation to be performed without using an autofocus only computer.

(3) Automatic Shooting Function (Automatic Flash Photographing Function)

The board computer 316 analyzes a state of the alignment luminescent spots AL (310, 310) and the split luminescent lines SL (311, 311) on a video signal to be obtained from the CCD 37a of the observation CCD camera 37 and performs automatic flash photographing. Similar to the autofocus function described above, analyzing a video signal on the board computer 316 enables an automatic shoot operation to be performed without using an automatic shoot only computer.

(4) Automatic Small Pupil Switching Function

The board computer 316 analyzes a state of the split luminescent lines SL (311, 311) of a video signal to be obtained from the CCD 37a of the observation CCD camera 37 and performs an automatic small pupil switching operation which automatically inserts a small pupil aperture when an eye to be examined has a small pupil. Similar to the autofocus function described above, analyzing a video signal on the board computer 316 enables an automatic shoot operation to be performed without using a computer only for automatic small pupil switching.

(5) Monitor Display Function

The board computer 316 displays an observation image and a photographed image of the observation CCD camera 37 on the monitor 31.

(6) Pseudo Target Display Function

The board computer 316 superimposes and displays a pseudo split target at a position of a split target of an optical image. It also superimposes and displays a pseudo alignment target at a position of an alignment target of the optical image.

The DC power supply 318 serves the following functions:

(1) The DC power supply PCB 318 controls light emission of the halogen lamp 17b by the halogen lamp control section 318a.

(2) The DC power supply PCB 318 controls light emission of the xenon lamp 17a by the xenon lamp control section 318b.

Figure 6:
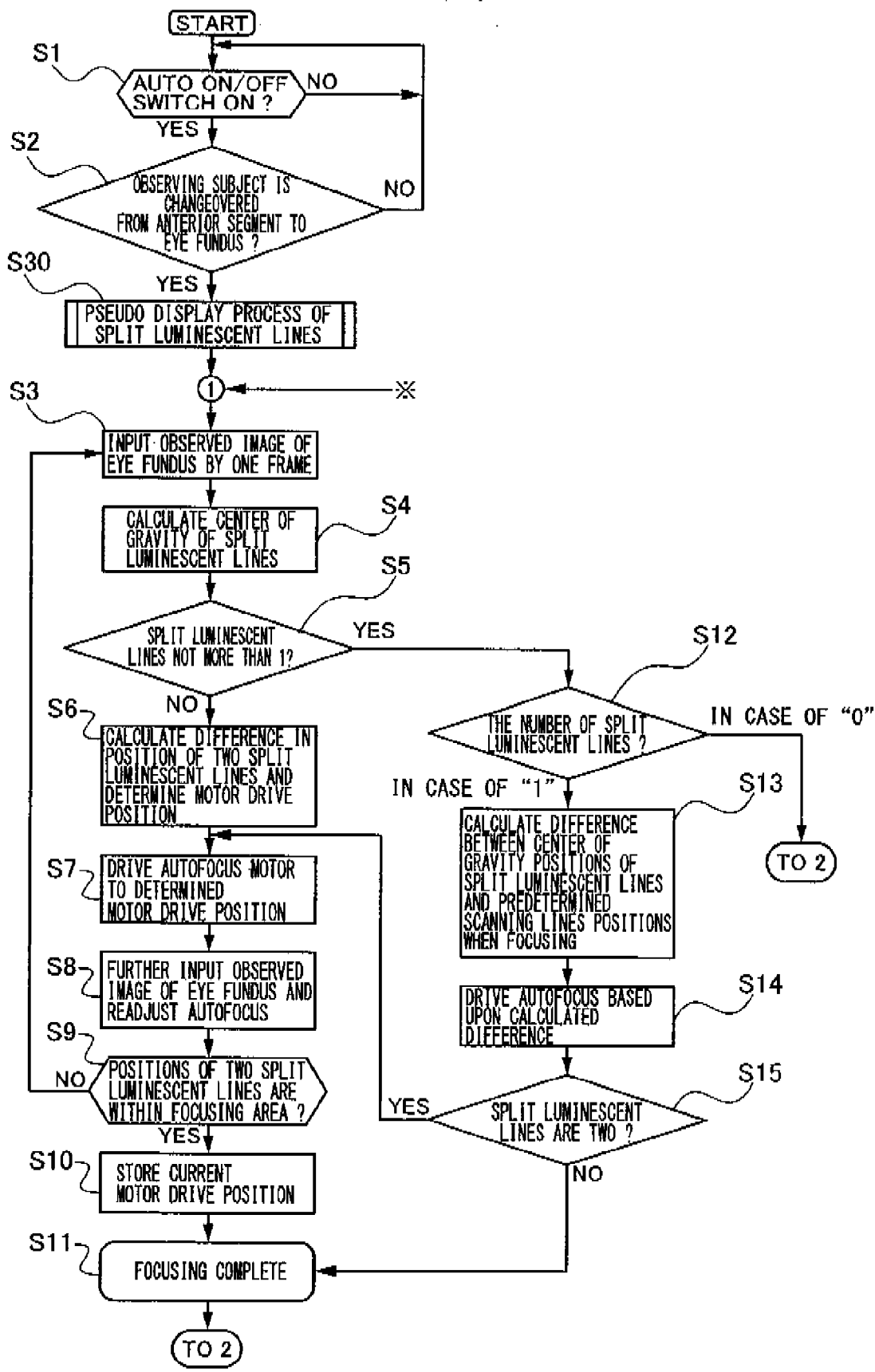
FIG. 6 shows a flow chart of an auto focus operation which is carried out on a board computer 316 of the non-mydriasis fundus camera of the first example according to the invention.
Figure 7:
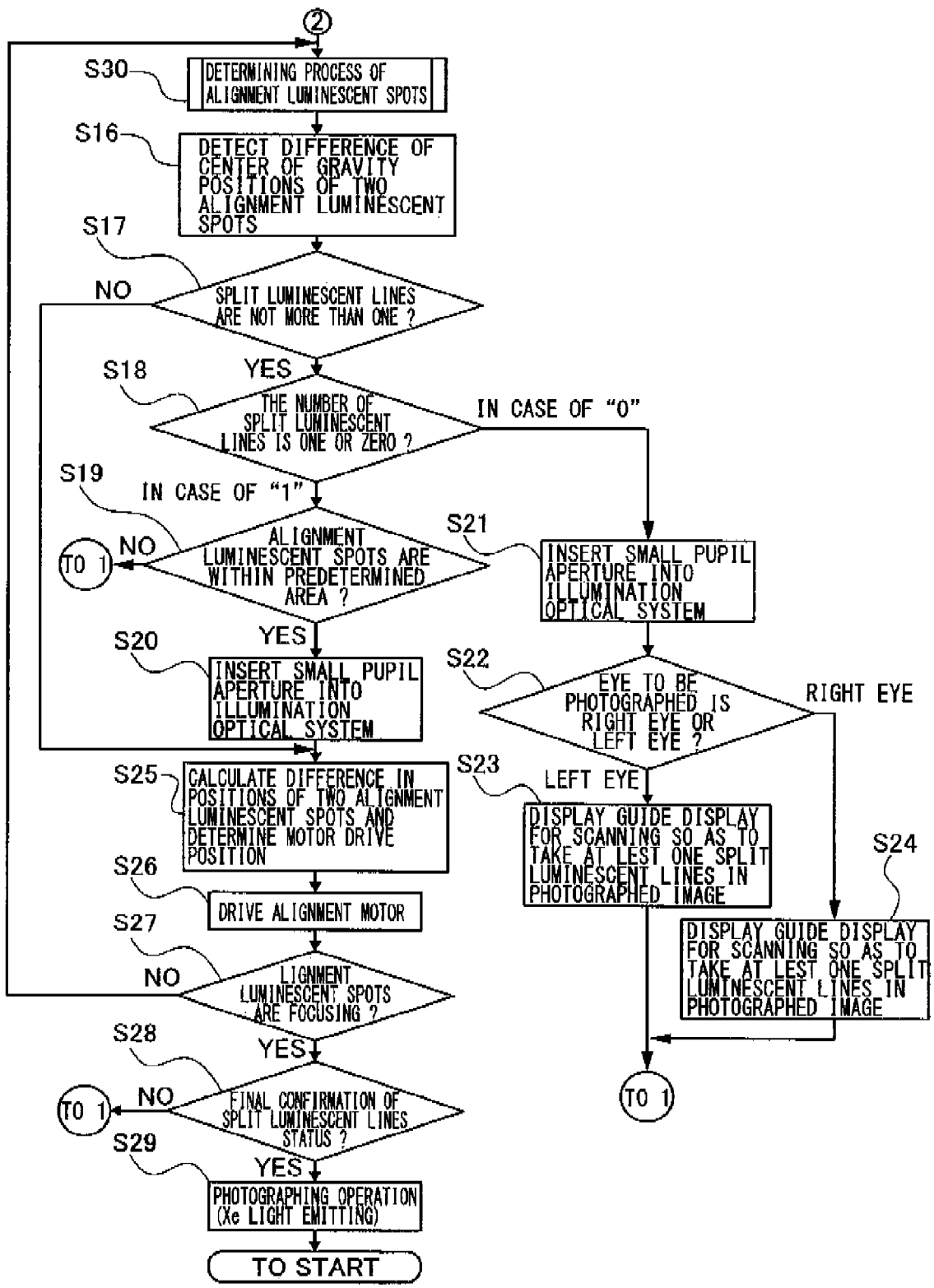
FIG. 7 shows a flow chart of a shute operation which is carried out on the board computer 316 of the non-mydriasis fundus camera of the first example according to the invention.

FIG. 6 is a flow chart of an autofocus control operation to be carried out on the board computer 316 of the non-mydriasis fundus camera of the working example 1. FIG. 7 is a flow chart of an auto shoot control operation to be carried out on the board computer 316 of the non-mydriasis fundus camera of the working example 1 (including a repetition of autofocus control operations). Respective steps of the flow charts of FIG. 6 and FIG. 7 representing the operations of an automatic photographing control section will be described hereinafter.

In step S1, it is determined whether an automatic ON/OFF switch 213 is an ON state. If it is determined that the automatic ON/OFF switch 213 is in ON state, the flow proceeds to step S2. On the one hand, if it is determined that the automatic ON/OFF switch 213 is in an OFF state, the flow repeats the determination at step S1.

In step S2, following the determination in step S1 (the determination that the automatic ON/OFF switch is in an ON state), it is determined whether or not an observation object has switched from an anterior eye segment to an eye fundus. If it is determined that the observation object has switched from the anterior eye segment to the eye fundus, the flow proceeds to step S3. On the one hand, if it is determined that the observation object remains as the anterior eye segment or that it remains as the eye fundus, the flow returns to step S1.

Figure 8:
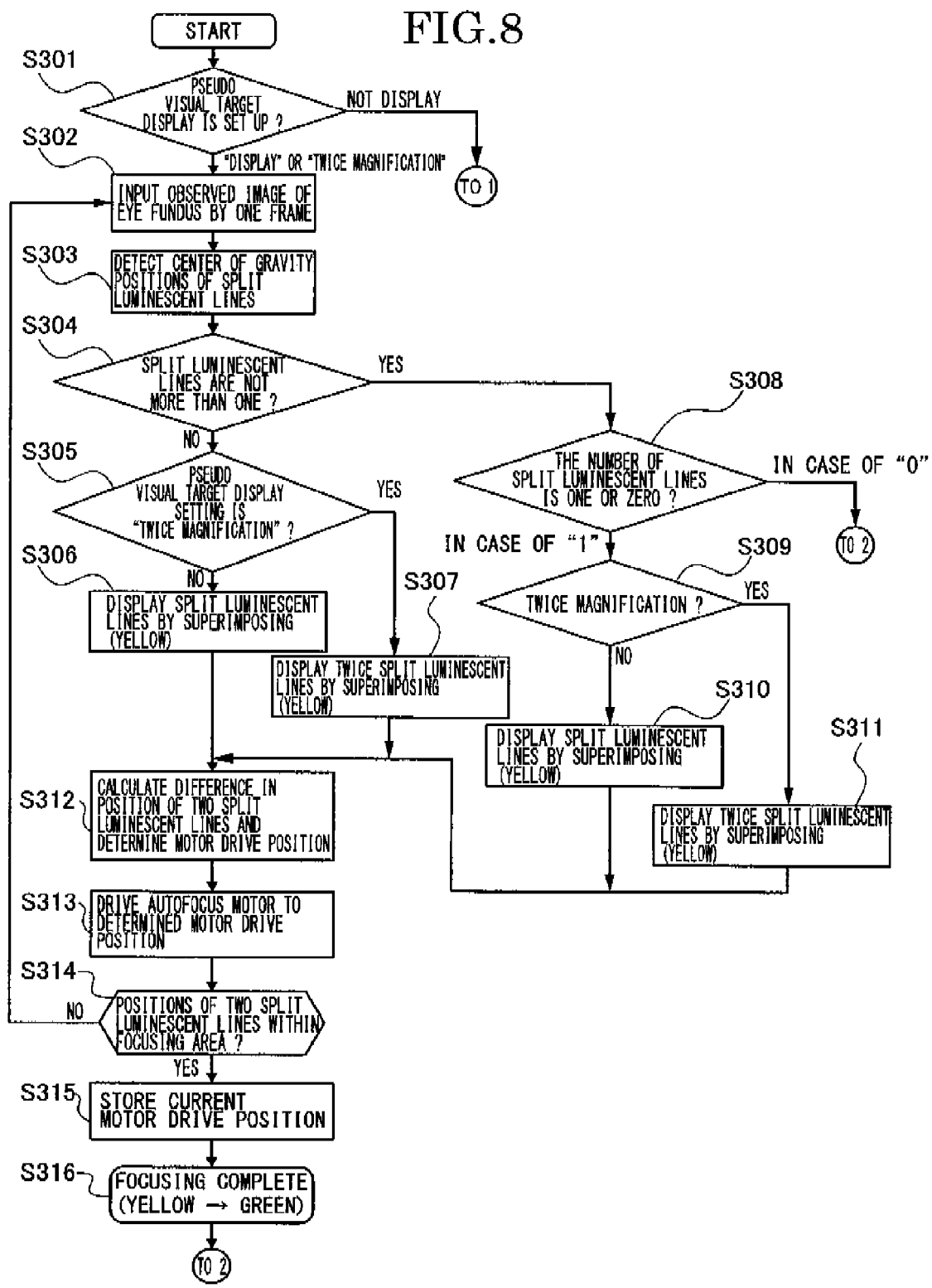
FIG. 8 shows a flow chart of a pseudo display process of split luminescent lines SL which is carried out at Step (S30) during an auto focus operation of the board computer 316 of the non-mydriasis fundus camera of the first example according to the invention.

In step S30, following the determination in step S2 (the determination that the observation object has switched from the anterior eye segment to the eye fundus), a pseudo display process of split luminescent lines is performed according to the flow chart shown in FIG. 8.

In step S3, following selection of a display state in step S30 (selection by the pseudo visual setting part 218 that there is no pseudo display of the split luminescent lines SL), only one frame of an eye fundus image to be obtained from a CCD 37a of an observation camera 37 is captured through a capture board 319, and the flow proceeds to step S4, In step S4, following the capturing of the observation image of the eye fundus in step S3, a centroid position of the split luminescent lines SL is detected to carry out an autofocus by the split luminescent lines SL of the optical image, and the flow proceeds to step S5. Here, in the detection of a centroid position of split luminescent lines SL, a center of an area where intensity exceeds a threshold in the luminance distribution characteristic of the split luminescent lines SL in the observation image of the eye fundus captured in step S3 is made a centroid position.

In step S5, following the detection of the centroid position of the split luminescent lines SL in step S4, it is determined whether or not the number of the split luminescent lines SL is less than or equal to 1. If it is determined that the number of split luminescent lines SL is not less than or equal to 1 (2 lines), the flow proceeds to the step S6. On the one hand, if it is determined that the number of the split luminescent lines SL is less than or equal to 1, the flow proceeds to step S12. Here, the number of centroid positions detected by using the luminance distribution characteristic in step S4 is used for the number of the split luminescent lines.

In step S6, following the determination on the number of the split luminescent lines (the determination that the number of the split luminescent lines is 2) in step S5 or in step S15 to be described later, a difference between the two centroid positions of the two split luminescent lines SL (311, 311) is calculated, a drive position of an autofocus motor 332 is determined, and the flow proceeds to step S7. Here, based on a vertical positional relationship of the right and left split luminescent lines SR (311, 311), a motor drive direction is also determined together with the motor drive position.

In step S7, following the determination of the motor drive position in step S6, an auto focus motor 332 (focusing motor) is driven at the determined motor drive position and in the determined motor drive direction, and the flow proceeds to step S8.

In step S8, following the driving of the auto focus motor 332 in step S7, only one frame of an observation image of an eye fundus from the CCD 37a of the observation CCD camera 37 is captured by way of the capture board 319. When a misalignment of the two split luminescent lines SL (311, 311) in the captured observation image of the eye fundus is recognized, fine adjustment is carried out by using the autofocus motor 332 so that the two split luminescent lines SL (311, 311) can be aligned, and the flow proceeds to step S9.

In step S9, following the fine adjustment of the autofocus in step S8, it is determined whether or not the positions of the two split luminescent lines SL (311, 311) are within a focusing range. If it is determined that the positions of the two split luminescent lines SL (311, 311) are within the focusing range, the flow proceeds to step S10. On the one hand, if it is determined that the positions of the two split luminescent lines SL (311, 311) are out of the focusing range, the flow returns to step S3. Here, when a separation amount of the two split luminescent lines SL (311, 311) is within ±0.5 D (split separation amount ⅛), it is determined that the positions of the two split luminescent lines SL (311, 311) are within the focusing range.

In step S10, following the determination on the positions of the split luminescent lines SL in step S9 (the determination that the positions of the two split luminescent lines SL (311, 311) are within the focusing range), a current motor drive position of the autofocus motor 332 is stored, and the flow proceeds to step S11.

In step S11, following the storage of the current motor drive position in step S10 or the determination of the number of the split luminescent lines SL in step S15 (the determination that the number of split luminescent lines recognized by the observation image of the eye fundus is 1), it is considered that the focusing by the autofocus operation has completed, and the flow proceeds to step S16 in which a small pupil detection operation or an automatic shoot operation starts.

In step S12, following the determination on the number of the split luminescent lines SL in step S5 (the determination that the number of the split luminescent lines SL is less than or equal to 1), it is determined whether or not the number of the split luminescent lines SL is 1 or 0. If the number of the split luminescent lines SL is 1, the flow proceeds to step S13. On the one hand, if the number of the split luminescent lines SL is 0, the flow proceeds to step S16 where the small pupil detection operation starts.

In step S13, following the determination on the number of the split luminescent lines in step S12 (the determination that the number of the split luminescent lines SL is 1), a difference between a centroid position of the split luminescent lines SL and a predetermined position of a scanline during focusing is calculated, and the flow proceeds to step S14.

In step S14, following the calculation in step S13 (the calculation of the difference between the centroid position of the split luminescent lines SL and the predetermined position of the scanline during focusing), the autofocus motor 332 (focusing motor) is driven according to the motor drive position and the motor drive direction based on the calculated difference, and the flow proceeds to step S15. Here, the motor drive direction is determined based on which split luminescent line of the right and left split luminescent lines SL has been detected.

In step S15, following the driving of the focusing motor in step S14, only one frame of the observation image of the eye fundus is captured again to determine the number of the split luminescent lines SLs recognized in the observation image of the eye fundus. If it is determined that the number of the split luminescent lines SL is 2, the flow proceeds to step S6. On the one hand, if it is determined that the number of the split luminescent lines SL is 1, the flow proceeds to step S11.

In step S16, following the completion of focusing in step S11, the determination on the number of the split luminescent lines SL in step S12 (the determination that the number of the split luminescent lines SL recognized in the observation image of the eye fundus is 1 or 0), or a determination on a match of alignment luminescent spots AL in step S27 to be described later (the determination that the two alignment luminescent spots AL do not match), an observation image of an eye fundus obtained from the CCD 37a of the observation CCD camera 37 is captured, a centroid position of the two alignment luminescent spots is detected from the captured observation image of the eye fundus, and the flow proceeds to step S17. Here, in the detection of the centroid position of the alignment luminescent spots AL, similar to the split luminescent lines SL, a center of an area where luminance exceeds a threshold in the luminance distribution characteristic of the alignment luminescent spots AL in the captured observation image of the eye fundus is detected as a centroid position.

In step S17, following the detection of the centroid position of the two alignment luminescent spots in step S16, it is determined whether or not the split luminescent lines SL recognized by the observation image of the eye fundus is less than or equal to 1. If it is determined that the number of the split luminescent lines SL is less than or equal to 1 (1 or 0), the flow proceeds to the step S18. On the one hand, if it is determined that the number of the split luminescent lines 311, 311 is 2, the flow proceeds to step S25.

In step S18, following the determination on the number of the split luminescent lines SL in step S17 (the determination that the number of the split luminescent lines SL recognized in the observation image of the eye fundus is less than or equal to 1), it is determined whether the number of the split luminescent lines SL recognized in the observation image of the eye fundus is either 1 or 0. If it is determined that the number of the split luminescent lines SL is 1, the flow proceeds to step S19. On the one hand, if it is determined that the number of the split luminescent lines SL is 0, the flow proceeds to step S21.

In step S19, following on the determination on the number of the split luminescent lines SL in step S18 (the determination that the number of the split luminescent lines SL is 1), it is determined whether two alignment luminescent spots (310, 310) exist in a predetermined position, that is to say, in the inner side of ( ) scale 309. If it is determined that the two alignment luminescent spots AL (310, 310) exist in the inner side of the ( ) scale 309, the flow proceeds to step S20. On the one hand, if it is determined that the two alignment luminescent spots AL (310, 310) exist in the outer side of the ( ) scale 309, the flow returns to step S3.

In step S20, following the determination in step S19 (the determination that the two alignment luminescent spots AL (310, 310) exist in the in the ( ) scale 309), a small pupil aperture (liquid crystal body aperture) AP is inserted into the illumination optical system, and the flow proceeds to step S25. That is to say, it is determined that an eye to be examined has a small pupil based on that the split luminescent line SL recognized in the observation image of the eye fundus is 1, and the small pupil aperture AP is automatically inserted provided that alignment adjustment within the allowable range is performed. At a high magnification change (angle of view of 30°), for example, the small pupil aperture AP is inserted into the illumination optical system, thereby enabling a pupil diameter up to ⌀3.3 mm to be photographed. In addition, if the small pupil aperture AP is inserted at the high magnification change, an electronic mask to be described later is set as a measure against flare.

In step S21, following the determination on the number of the split luminescent lines SL in step S18 (the determination that the number of the split luminescent lines SL is 1), similar to step S20, the small pupil aperture AP is inserted into the illumination optical system, and the flow proceeds to step S22.

In step S22, following the insertion of the small pupil aperture AP in step S21, it is determined whether an eye to be photographed is a right eye or a left eye. If it is determined that the eye to be photographed is a left eye, the flow proceeds to step S23. On the one hand, if it is determined that the eye to be photographed is a right eye, the flow proceeds to step S24.

In step S23, following the determination that the eye to be photographed is the left eye in step S22, an instruction for guiding an examiner to an alignment change so that even 1 of the split luminescent lines SL enters the image of the left eye is displayed, and the flow proceeds to step S23. Here, a guiding instruction is displayed by moving the ( ) scale 309 by a distance corresponding to 0.5 mm, on a left eye image of an examinee.

In step S24, following the determination that the eye to be photographed is the right eye in step S22, an instruction for guiding an examiner to an alignment change so that even 1 of the split luminescent lines SL enters the image of the right eye is displayed, and the flow proceeds to step S3. Here, a guiding instruction is displayed by moving the ( ) scale 309 by a distance corresponding to 0.5 mm, on the right eye image of the examinee.

In step S25, following the determination on the number of the split luminescent lines SL in step S17 (the determination that the number of the split luminescent lines SL is 2) or the insertion of the small pupil aperture AP into the illumination optical system in step S20, a difference between centroid positions of the two alignment luminescent spots AL is calculated, a motor drive position by the alignment motor 330 is determined based on the calculated centroid position, and the flow proceeds to step S26. Here, a motor drive direction (vertical, right/left, forward/backward) is determined based on a positional relationship of the two alignment luminescent spots AL (310, 310) with respect to the ( ) scale 309.

In step S26, following the determination on the motor drive position in step S25, the alignment motor 330 is driven at the determined motor drive position in the determined motor drive direction, and the flow proceeds to step S27.

In step S27, following the driving of the alignment motor 330 in step S26, it is determined whether or not the two alignment luminescent spots AL (310, 310) match in the ( ) scale 309. If it is determined that the two alignment luminescent spots AL (310, 310) match in the ( ) scale 309, the flow proceeds to step S28. On the one hand, if it is determined that the two alignment luminescent spots AL (310, 310) do not match in the ( ) scale 309, the flow returns to step S16. Here, in the determination on the match of the two alignment luminescent spots AL (310, 310), it is determined that the two alignment luminescent spots AL (310, 310) match on condition that a difference between centroid positions of the two alignment luminescent spots AL (310, 310) is less than or equal to a predetermined amount (0.3 mm, for example), or on condition that a luminescent point separation is within a predetermined amount (⅙, for example).

In step S28, following the determination on the match of the alignment luminescent spots AL in step S27, it is determined whether or not final confirmation of a state of the split luminescent lines SL has finished. If it is determined that the final confirmation of the state of the split luminescent lines SL has finished, the flow proceeds to step S29. On the one hand, if it is determined that the final confirmation of the state of the split luminescent lines SL has not finished, the flow returns to step S3. Here, in the final confirmation of the state of the split luminescent lines SL, similar to the step S9, it is determined that the final confirmation of the state of the split luminescent lines SL has finished if the positions of the two split luminescent lines SL (311, 3311) are within the focusing range, while it is determined that the final confirmation of the state of the split luminescent lines SL has not finished if the positions of the two split luminescent lines (311, 311) are out of the focusing range.

In step S29, following the determination that the final confirmation of the state of the split luminescent lines SL has finished in step S28, a photographing operation of an eye fundus by an automatic shoot function is carried out. That is to say, the shutter of a photographing CCD camera (camera) 6 is released while automatically lighting on the xenon lamp 17a, and the flow return to the start.

FIG. 8 is a flow chart of a pseudo display process of split luminescent lines SL to be carried out in step S30 while a board computer 316 of the non-mydriasis fundus camera of the working example 1 is in an autofocus control operation (pseudo display processing means).

In step S301, it is determined whether a pseudo target display setting part 218 selects "not to display" a pseudo display or it selects "to display" the pseudo display or selects "double size". If "not to display" is selected, the flow proceeds to step S3 of FIG. 6. On the one hand, if "to display" or "double size" is selected, the flow proceeds to step S302.

In step S302, following the determination on the selection of the pseudo target display setting part 218 in step S300 (the determination that the pseudo target setting part 218 has selected "to display" or "double size"), only one frame of the observation image of the eye fundus to be obtained from the ccd 37a of the observation CCD camera 37 is captured by way of the capture board 319, and the flow proceeds to the step S303.

In step S303, following the capturing of the observation image of the eye fundus in step S302, a centroid position of the split luminescent lines SL is detected, and the flow proceeds to step S304. Here, in the detection of the centroid position of the split luminescent lines SL, a center of an area where luminance exceeds a threshold in the luminance distribution characteristic of the captured observation image of the eye fundus is detected as a centroid position.

In step S304, following the detection of the centroid position of the split luminescent lines SL in step S303, it is determined whether or not the number of the split luminescent lines SL is less than or equal to 1. If it is determined that the number of the split luminescent lines SL is 2, the flow proceeds to step S305. On the one hand, if it is determined that the number of the split luminescent lines SL is less than or equal to 1, the flow proceeds to step S308. Here, in the determination on the number of the split luminescent lines SL, the number of the centroid positions detected by using the luminance distribution characteristic in step S303 is used.

In step S305, following the determination on the number of the split luminescent lines SL in step S304 (the determination that the number of split luminescent lines SL is 2), it is determined whether or not "double size" is selected by the pseudo target display setting part 218. If "to display" is selected by the pseudo target display setting part 218, the flow proceeds to the step S306. On the one hand, "double" size is selected by the pseudo target display setting part 218, the flow proceeds to step S307.

In step S306, following the determination that "to display" is selected in step S305, pseudo split luminescent lines SLV (311V, 311V) having a shape in same size as or a litter larger shape similar to the split luminescent lines SL (311, 311) are superimposed and displayed at the positions of the split luminescent lines SL (311, 311) detected in step S303, and the flow proceeds to step S312. Here, color tone of the pseudo split luminescent lines SLV (311V, 311V) will be yellow.

In step S307, following the determination that "double size" is selected in step S305, pseudo split luminescent lines SLV (311V, 311V) of double size of and having a shape similar to the split luminescent lines SL (311, 311) are superimposed and displayed at the positions detected in step S303, and the flow proceeds to step S312. For example, if the split luminescent lines SL (311, 311) are 8-pixel wide, the pseudo split luminescent line shall be 16-pixel wide. In addition, the color tone of the pseudo split luminescent lines SLV (311V, 311V) will be yellow.

In step S308, following the determination that the number of the split luminescent lines SL is less than or equal to 1 in step S304, it is determined whether the number of the split luminescent lines SL is 1 or 0. If it is determined that the number of the split luminescent lines SL is 1, the flow proceeds to step S309. On the one hand, if the number of the split luminescent lines SL is 0, the flow proceeds to step S16 of FIG. 7.

In step S309, following the determination that the number of the split luminescent lines SL is 1 in step S308, it is determined whether or not "double size" is selected by the pseudo target display setting part 218. If "to display" is selected by the pseudo target display setting part 218, the flow proceeds to step S310. On the one hand, if "double size" is selected by the pseudo target display setting part 218, the flow proceeds to step S311.

In step S310, following the determination that "to display" is selected in step S309, pseudo split luminescent lines SLV (311V, 311V) having a shape in same size as or a slightly larger shape similar to the split luminescent lines SL (311, 311') are superimposed and displayed at the position of the one split luminescent lines (31) detected in step S303 and at an estimated position of the other split luminescent line (311'), and the flow proceeds to step S312. Here, a position of the other one split luminescent line SL (311') is estimated based on a symmetry axis of the two split luminescent lines SL (311, 311) at a focusing position of a predetermined split luminescent lines SL, and the position of the detected one split luminescent line (311). In addition, a color tone of the pseudo split luminescent lines SL (311V, 311V) will be yellow.

In step S311, following the determination that "double size" is selected in step S309, pseudo split luminescent lines SLV (311V, 311V) having a double size of and a shape similar to the split luminescent lines SL (311, 311') are superimposed and displayed at the position of the one split luminescent line SL (311) detected in step S303 and the position of the estimated other one split luminescent line SL (311'), and the flow proceeds to step S312. For example, if the split luminescent lines SL (311, 311') are 8-pixel wide, the pseudo split luminescent lines SLV (311V, 311V) will be 16-pixel wide. In addition, a color tone of the pseudo split luminescent lines SLV (311V, 311V) will be yellow.

In step S312, following the superposition and display of the pseudo split luminescent lines SLV (311V, 311V) in step S306, step S307, step S310, or step S311, a difference between centroid positions of the two pseudo split luminescent lines SLV (311V, 311V) is calculated, a motor drive position by the auto focus motor 332 is determined based on the calculated difference of centroid positions, and the flow proceeds to step S313. Here, a motor drive direction is also determined together with the motor drive position, based on a vertical positional relation of the right and left pseudo split luminescent lines SLV (311V, 311V).

In step S313, following the determination of the motor drive position in step S312, the autofocus motor 332 (focusing motor) is driven at the determined motor drive position and in the determined motor drive direction, and the flow proceeds to step S314.

In step S314, following the driving of the autofocus motor 332 in step S313, it is determined whether or not positions of the two pseudo split luminescent lines SLV (311V, 311V) are within a focusing range. If it is determined that the positions of the two pseudo split luminescent lines SLV (311, 311V) are in the focusing range, the flow proceeds to step S315. On the one hand, if it is determined that the two pseudo split luminescent lines SLV (311V, 311V) are out of the focusing range, the flow returns to step S302. Here, it is determined that the positions of the two pseudo split luminescent lines SLV (311V, 311V) are within the focusing range when a separation amount of the two pseudo split luminescent lines SLV (311V, 311V) is within ±0.5 D (split separation amount ⅛).

In step S315, following the determination that the positions of the two pseudo split luminescent lines SLV (311V, 311V) are within the focusing range in step S314, a current motor drive position of the autofocus motor 332 is stored and the flow proceeds to step S316.

In step S316, following the storage of the current motor drive position in step S315, it is considered that the focusing has completed by the autofocus operation, a color tone of the two pseudo split luminescent lines SLV (311V, 311V) changes from yellow to green, and the flow proceeds to step S16 where the small pupil detection operation or the automatic shoot function operation starts.

The operations in the non-mydriasis fundus camera of the working example 1 will be described by dividing them to an eye fundus photographing operation by manual operation, an autofocus operation when pseudo display is not selected, an autofocus operation when the pseudo display is selected, an automatic shoot operation when the two split luminescent lines are recognized, an automatic shoot operation during determination on a small pupil, and a split luminescent line guiding operation.

[Eye Fundus Photographing Operation by Manual Operation]

Figure 9A:
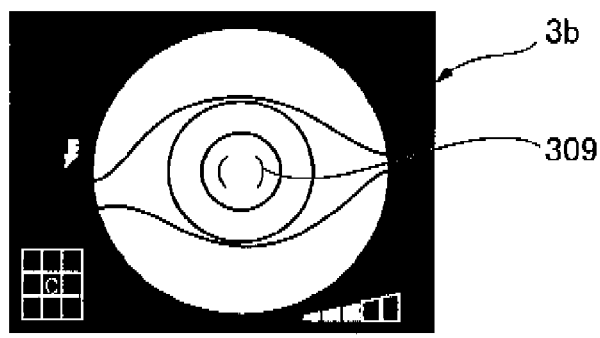
FIG. 9A shows an explanation view of an eye fundus photographing operation by manual operation when an auto ON/OFF switch of the non-mydriasis fundus camera of the first example according to the invention is in an OFF state and also shows one example of a monitor screen in which an eye to be examined is displayed on a center part thereof.
Figure 9B:
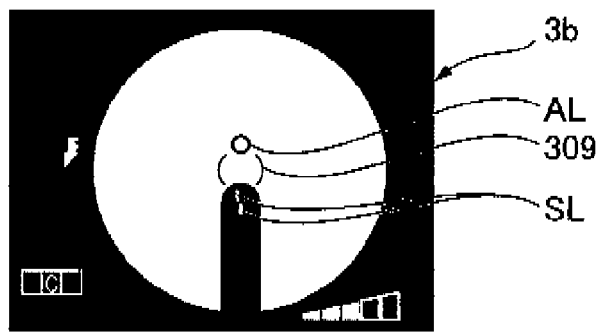
FIG. 9B shows an explanation view of the eye fundus photographing operation by manual operation when an auto ON/OFF switch of the non-mydriasis fundus camera of the first example according to the invention is in an OFF state and also shows one example of a monitor screen prior to performing a focusing operation and an alignment operation.
Figure 9C:
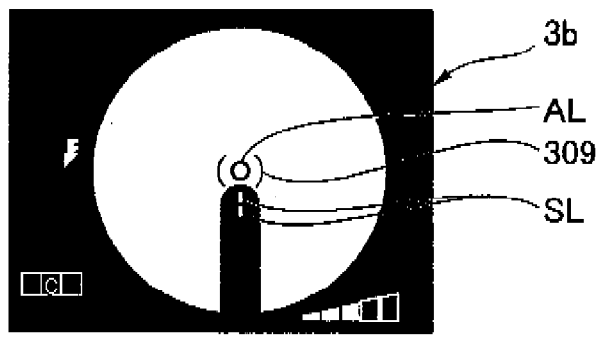
FIG. 9C shows an explanation view of an eye fundus photographing operation by manual operation when an auto ON/OFF switch of the non-mydriasis fundus camera of the first example according to the invention is in an OFF state and also shows one example of a monitor screen after the focusing operation and then alignment operation are performed.

FIG. 9A to D are explanation views of an eye fundus photographing operation by manual operation when an automatic ON/OFF switch of the non-mydriasis fundus camera of the working example 1 is in an OFF state. FIG. 9A shows a monitor screen in which an eye to be examined is displayed on a center part thereof. FIG. 9B shows a monitor screen before a focusing operation and an alignment operation are performed. FIG. 9C shows a monitor screen after the focusing operation and the alignment operation are performed.

Figure 9D:
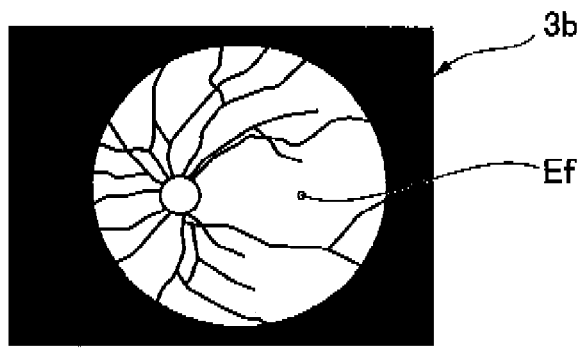
FIG. 9D shows an explanation view of an eye fundus photographing operation by manual operation when an auto ON/OFF switch of the non-mydriasis fundus camera of the first example according to the invention is in an OFF state and also shows one example of a monitor screen in which a review image of the eye fundus when photographing is displayed.

FIG. 9D shows a monitor screen 31 in which a photographed image of the eye fundus is displayed. The operating procedure in the case in which an examiner is skilled and a photographing of an eye fundus is carried out by manual operation will be described hereinafter.

(1) When the examiner turns on a power supply switch to turn an automatic ON/OFF switch 213 in an OFF state, an observation screen appears after an opening screen is displayed on the monitor.

(2) The examiner moves a device main body 3 to the nearest side with a joy stick 2b and instructs an examinee who places his/her chin on a chin rest 4 to look straight ahead.

(3) The examiner moves the device main body horizontally or vertically with the joy stick 2b, and adjusts a position of the device main body 3 so that an eye to be examined E appears in the center of an observation monitor 3b, as shown in FIG. 9A.

(4) The examiner aligns a ( ) scale 309 with a pupil of the examinee on the monitor 31 and checks whether size of the examinee's pupil is larger than the ( ) scale 309, that is, whether or not an eye fundus can be photographed, as shown in FIG. 9A.

(5) When the examiner moves the device main body 3 straight to the examinee side with the joy stick 2b, 2 alignment luminescent spots AL (310, 310) for W alignment of working distance W appear on the monitor 31. The examiner matches the two alignment luminescent spots AL (310, 310) to one, as shown in FIG. 9B. Then, the examiner instructs the examinee to look at green flash (internal fixed target).

(6) By operating a focusing handle 3a, the examiner aligns two split luminescent lines SL (311, 311) (see FIG. 9B) in a vertical direction, as shown in FIG. 9C. Then, by operating the joy stick 2b, he/she places the two alignment luminescent spots AL (310, 310) in the ( ) scale 309.

(7) After confirming the alignment of the split luminescent lines SL (311, 311) and the match of the alignment luminescent spots AL (310, 310), the examiner presses a photographing switch 2c provided at the upper end of the joy stick 2c. Then, together with light emission of a xenon lamp 17a, a shutter of an imaging CCD camera (camera) is released, and an eye ground is photographed. After the eye ground photographing, a photographed eye ground image appears on the monitor 31, as shown in FIG. 9D.

(8) The examiner checks the photographed image of the eye ground and presses the photographing switch 2c again if he/she performs photographing. Through this operation, a screen to be displayed on the monitor 31 returns to an observation screen. Thus, he/she performs next photographing by repeating the steps (2) to (7) described above. In addition, if the examiner wishes to delete a photographed eye fundus image after photographing the eye fundus, he/she presses an image deletion switch 207 with the eye fundus image displayed on the monitor 31. Through this operation, the eye fundus image displayed on the monitor is deleted and the screen on the monitor 31 returns to the observation screen.

When an eye fundus is photographed by this manual operation, pseudo alignment luminescent spots ALV (310V, 310V) or pseudo split luminescent lines SLV (311V, 311V) can be superimposed at positions of the detected alignment luminescent spots AL (310, 310) or split luminescent lines SL (311, 311) and displayed on the monitor 31. In this case, since the pseudo alignment luminescent spots ALV (310V, 310V) and the pseudo split luminescent lines SLV (311V, 311V) are displayed by superimposing them at the positions of the original alignment luminescent spots AL (310, 310) and split luminescent lines SL (311, 311), the alignment adjusting operation with the pseudo alignment luminescent spots ALV (310V, 310V) and the focusing operation with the pseudo split luminescent lines SLV (311, 311V) can be carried out, similar to an alignment adjusting operation with the original alignment luminescent spots (310, 310) and the focusing operation with the original split luminescent lines SL (311, 311). In addition, since targets (pseudo alignment luminescent spots ALV and pseudo split luminescent line SLV) to be displayed have higher luminance than original targets (alignment luminescent spots AL and split luminescent lines SL), which are optical images, visibility of the targets will increase and an alignment adjusting operation and a focusing operation become easier compared with a case in which an alignment adjusting operation and a focusing operation are carried out while looking at the original targets which are optical images.

[Autofocus Action when Pseudo Display is not Selected]

Figure 10:
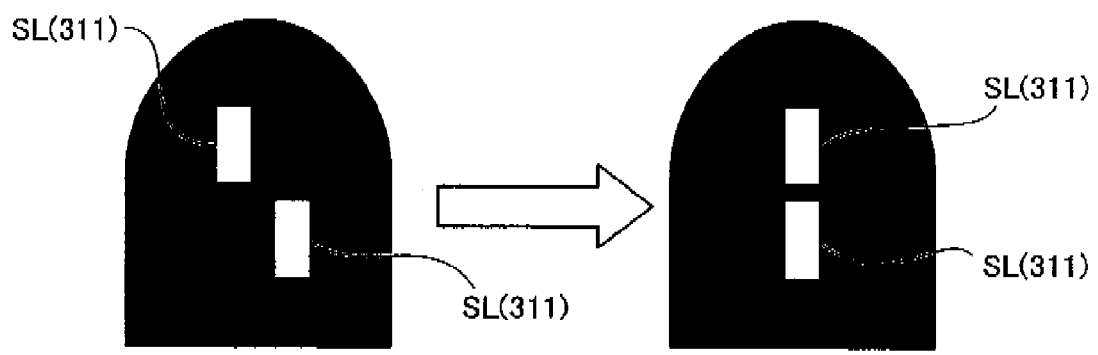
FIG. 10 shows an explanation view of a focusing operation using split luminescent lines in the non-mydriasis fundus camera of the first example according to the invention (when the auto ON/OFF switch is in an ON state and a pseudo display is not selected)
Figure 11:
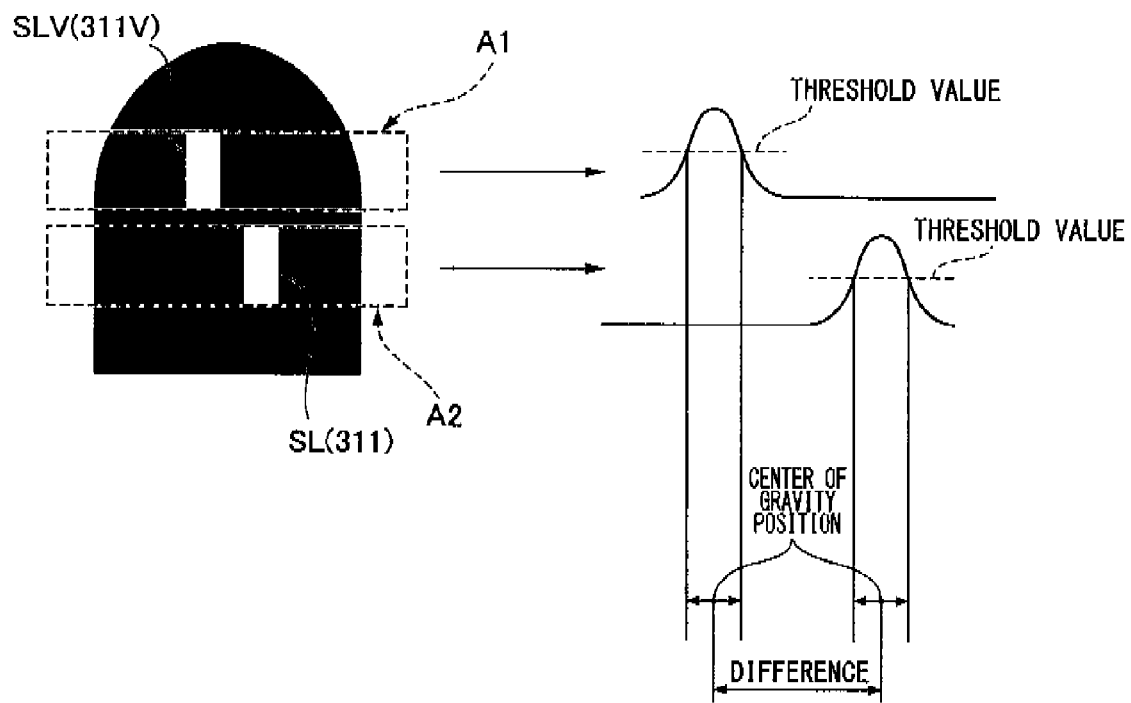
FIG. 11 shows an explanation view of a centroid position detecting operation using the split luminescent lines in the non-mydriasis fundus camera of the first example according to the invention (when the auto ON/OFF switch is in an ON state and the pseudo display is not selected)

FIG. 10 is an explanation view of an autofocus operation when an eye fundus is automatically photographed in the case in which an automatic ON/OFF switch 213 of the non-mydriasis fundus camera of the working example 1 is in an ON state and a pseudo display is not selected. FIG. 11 is an explanation view of a centroid position detecting operation of split luminescent lines during automatic photographing of an eye fundus in the case in which the automatic ON/OFF switch 213 of the non-mydriasis fundus camera of the working example 1 is in an ON state and the pseudo display is not selected. The autofocus operating procedure in the case in which an examiner is not skilled and an eye fundus is photographed by an automatic eye fundus photographing mode will be described hereinafter.

An autofocus operation in an automatic eye fundus photographing mode is an operation for aligning 2 separate split luminescent lines (311, 311) in a vertical direction, as shown in FIG. 10, by driving an autofocus motor 332 instead of a manual operation by a focusing handle 3a.

When a power switch is turned on by the examiner, the automatic ON/OFF switch 213 turns ON, an object to be photographed is switched from an anterior eye segment photographing to eye fundus photographing, and "not to display" is selected at a pseudo target display setting part 218, the flow of the autofocus operation proceeds from step S1->step S2->step S30->step S3->step S4 in the flow charge of FIG. 6. In step S3, only one frame of an observation image of an eye fundus is captured from a CCD 37a of an observation CCD camera 37 by way of a capture board 319 into a board computer 316. In the following step S4, a centroid position of the split luminescent lines SL is detected for the autofocus operation.

Now, detection of the centroid position of the split luminescent lines SL is described. As shown in the left side of FIG. 11, areas A1, A2 are set which are wider than the split luminescent lines SL (311, 311) almost at a same level as the split luminescent lines SL (311, 311) in the captured observation image of the eye fundus. Then, as shown in the right side of FIG. 11, a center of an area where luminance exceeds a threshold in each luminance distribution characteristic of the areas A1, A2 is detected as a centroid position.

Then, if it is determined that the number of the detected centroid positions is two, that is to say, the number of the split luminescent lines SL is two (311, 311), the flow proceeds from step S4 to step S5->step S6->step S7->step S8->step S9 in the flow chart of FIG. 6. In step S6, a difference between the centroid positions of the two split luminescent lines SL (311, 311) is calculated (FIG. 11), and a motor drive position by the autofocus motor 332 is determined. In step S7, the autofocus motor 332 is driven at the determined motor drive position and in the determined motor drive direction. In step S8, only one frame of the observation image of the eye fundus is captured again. When a misalignment of the two split luminescent lines SL (311, 311) is recognized, the autofocus motor 332 carries out fine adjustment in such a direction that the two split luminescent lines SL (311, 311) can be aligned. In step S9, it is determined whether or not the two split luminescent lines SL (311, 311) are within the focusing range.

If it is determined in step S9 that the positions of the two split luminescent lines SL (311, 311) are within the focusing range, the flow proceeds from step S 10->step S11, where it is considered that focusing has completed and a next small pupil detection operation or automatic shoot function operation starts. In addition, if it is determined in step S9 that the positions of the two split luminescent lines SL (311, 311) are out of the focusing range, the flow returns to the step S3, where the autofocus operation described above will be repeated until it is determined that the positions of the two split luminescent lines SL (311, 311) are within the focusing range.

On the one hand, if it is determined that the detected centroid position is one, that is to say, the number of the split luminescent lines SL is one (311), the flow proceeds from step S4 to step S5->step S12->step S13->step S14->step S15 in the flow chart of FIG. 6. In step S12, it is determined whether the number of the split luminescent lines SL is one or zero. In step S13, a difference between the centroid position of the one split luminescent line SL (311) and a position of a scanline during predetermined focusing is calculated. In step S14, the autofocus motor 332 is driven at the motor drive position and the motor drive direction based on the calculated difference. In step S15, only one frame of the observation image of the eye fundus is captured again, and it is determined whether or not there are two split luminescent lines SL recognized in the observation image of the eye fundus.

Then, if it is determined in step S15 that there are two (311, 311) split luminescent lines SL, the flow proceeds to step S6, where an autofocus operation based on the two split luminescent lines SL (311, 311) will be carried out again. The reason for determining the number of the split luminescent lines in step S15 is that a focusing error will be larger when one split luminescent line is one. If it is determined in step S15 that the two split luminescent lines SL exist, the focusing error is kept low by performing the focusing operation (step S6 to step S8) with the two split luminescent lines SL (S311, S311).

In addition, if it is determined in step S15 that only one split luminescent line SL exists, the flow proceeds to the step S11 and it is considered that the focusing has completed. Then, the next small pupil detection operation or the automatic shoot function operation will start.

[Autofocus Action when Pseudo Display is Selected]

Figure 12A:
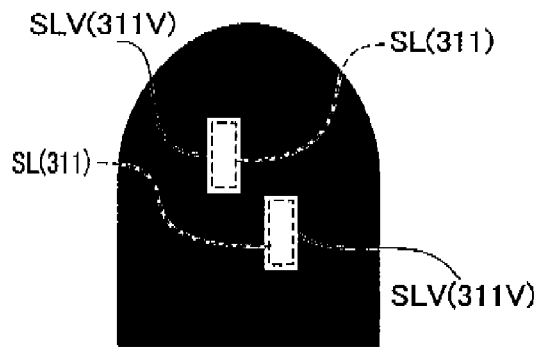
FIG. 12A shows en example view of pseudo split luminescent lines in the non-mydriasis fundus camera of the first example according to the invention (when the auto ON/OFF switch is in an ON state, the pseudo display is selected and two split luminescent lines of an optical image are detected)
Figure 12B:
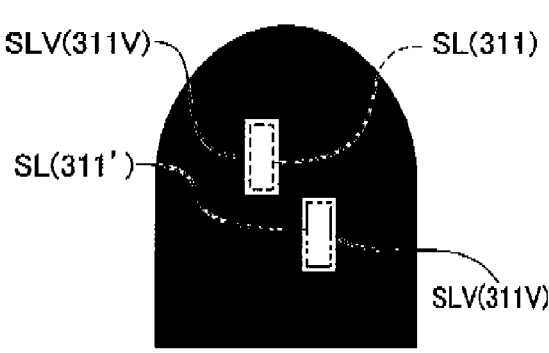
FIG. 12B shows a display example of the pseudo split luminescent lines in the non-mydriasis fundus camera of the first example according to the invention (when the auto ON/OFF switch is in an ON state, the pseudo display is selected and a one split luminescent line of the optical image is detected)
Figure 13:
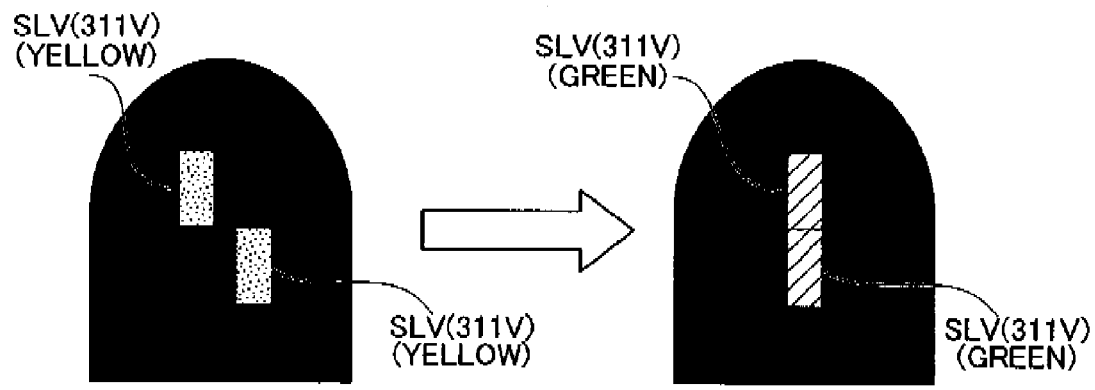
FIG. 13 shows a display example of the pseudo split luminescent lines when focusing in the non-mydriasis fundus camera of the first example according to the invention (when the auto ON/OFF switch is in an ON state and the pseudo display is selected)
Figure 14:
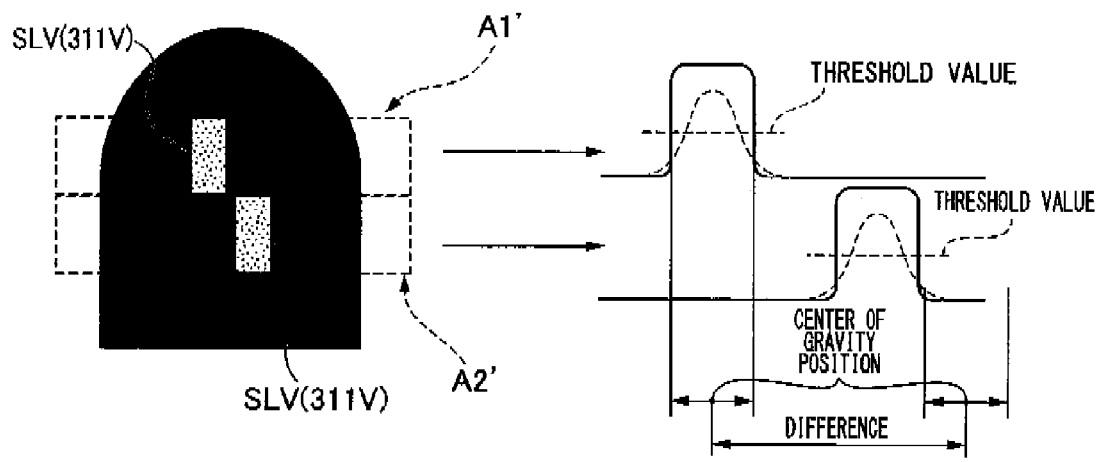
FIG. 14 shows an explanation view of the centroid position detecting operation using the split luminescent lines in the non-mydriasis fundus camera of the first example according to the invention (when the auto ON/OFF switch is in an ON state and the pseudo display is selected)

FIG. 12A and FIG. 12B are display examples of pseudo split luminescent lines when an automatic ON/OFF switch of the non-mydriasis fundus camera is in an ON state, and a pseudo display is selected. FIG. 12A shows a display example of pseudo split luminescent lines when two split luminescent lines SL (311, 311) are detected. FIG. 12B shows a display example of pseudo split luminescent lines when one split luminescent line SL (311) is detected. FIG. 13 is an explanation view of an autofocus operation when an eye fundus is automatically photographed, if the automatic ON/OFF switch of the non-mydriasis fundus camera of the working example 1 is in an ON state and a pseudo display is selected. FIG. 14 is an explanation view of a centroid position detection operation of pseudo split luminescent lines SLV (311V, 311V) when an eye fundus is automatically photographs, if the automatic ON/OFF switch of the non-mydriasis fundus camera of the working example 1 is in an ON state and the pseudo display is selected. The autofocus operating procedure in the case in which, for example, an examiner is not skilled, display of pseudo split luminescent lines SLV is selected, and an eye fundus is photographed in an automatic eye fundus photographing mode will be described.

An autofocus operation using pseudo split luminescent lines SLV in an automatic eye fundus photographing mode represents an operation for aligning spaced two pseudo split luminescent lines SLV (311V, 311V) in a vertical direction, as shown in FIG. 13, by driving the autofocus motor 332, instead of manual operation of using a focusing handle 3a.

When a power switch is turned on by the examiner, the automatic ON/OFF switch 213 turns ON, an object to be photographed is switched from an anterior eye segment photographing to eye fundus photographing, and "to display" or "double size" is selected by a pseudo target display setting unit 218, the flow proceeds from step S1->step S2->step S30 in the flowchart of FIG. 6, and pseudo display processing shown in the flow chart of FIG. 8 is performed.

When "to display" is selected by the pseudo target display setting unit 21B, and the split luminescent lines is two (311, 311), the flow proceeds from step S301->step S302->step S303->step S304->step S305->step S306 in the flow chart of FIG. 8. Then, in step S306, as shown in FIG. 12A, yellow pseudo split luminescent lines SLV (311V, 311V) having a similar shape slightly larger than the split luminescent lines SL (311, 311) are overlapped and displayed at the positions of the split luminescent lines SL (311, 311) detected in step S303.

When "double size" is selected by the pseudo target display setting unit 218, and the split luminescent lines is two (311, 311), the flow proceeds from step S301->step S302->step S303->step S304->step S305->step S307 in the flow chart of FIG. 8. Then, in step S307, yellow pseudo split luminescent lines SLV (311V, 311V) having a shape which is similar to but twice as large as the split luminescent lines SL (311, 311) of optical images are overlapped and displayed at the positions of the split luminescent lines SL (311, 311) detected in step S303.

When "to display" is selected by the pseudo target display setting unit 218, and the split luminescent line is one (311), the flow proceeds from step S301->step S302->step S303->step S304->step S308->step S309->step S310 in the flow chart of FIG. 8. Then, in the step S10, as shown in FIG. 12B, yellow pseudo split luminescent lines SLV (311V, 311V) having a similar shape slightly larger than the split luminescent lines SL (311, 311') are overlapped and displayed at the position of the one split luminescent lines SL (311) detected in step S303 and at the position of the other split luminescent line SL (311') estimated based on the e focusing position.

When "double size" is selected by the pseudo target display setting unit 218, and the split luminescent line is one (311), the flow proceeds from step S301->step S302->step S303->step S304->step S308->step S309->step S311 in the flow chart of FIG. 8. Then, in step S311, yellow pseudo split luminescent lines SLV (311V, 311V) having a similar shape which is twice as large as the split luminescent lines SL (311, 311') are overlapped and displayed at the position of the one split luminescent line St (311) detected in step S303 and at the other split luminescent line SL (311') estimated based on the focusing position.

When the pseudo split luminescent lines SLV (311V, 311V) are displayed, the flow proceeds from step S306 or step S307 or step S310 or step S311 to step S312->step S313->step S314 in the flow chart of FIG. 8. In step S312, a difference between centroid positions of the two pseudo split luminescent lines SLV (311V, 311V) is calculated (FIG. 14), and a motor drive position by the autofocus motor 332 is determined. In step S313, the autofocus motor 332 is driven at the determined motor drive position and the determined motor drive direction. In step S314, it is determined whether or not the positions of the two pseudo split luminescent lines SLV (311V, 311V) are within the focusing range.

In step S14, if it is determined that the positions of the two pseudo split luminescent lines SLV (311V, 311V) are within the focusing range, the flow proceeds from step S315->step S316. In step S316, it is considered that the focusing has completed, the pseudo split luminescent lines SLV (311V, 311V) have changed the color from yellow to green, as shown in FIG. 13, and a next small pupil detection operation or an auto shoot function operation starts. In addition, in step S314, if it is determined that the positions of the two pseudo split luminescent lines SLV (311V, 311V) are out of the focusing range, the flow returns to step S302, where the autofocus operation described above will be repeated until it is determined that the positions of the two pseudo split luminescent lines SLV (311V, 311V) are within the focusing range.

As described above, in step S312, a difference between centroid positions of the two pseudo split luminescent lines SLV (311V, 311V) is calculated. Then, as shown in the left side of FIG. 14, areas A1', A2' are set which are wider than the pseudo split luminescent lines SL (311V, 311V) almost at a same level as the overlapped and displayed pseudo split luminescent lines SL (311V, 311V). Then, as shown in the right side of FIG. 14, a center of an area where luminance exceeds a threshold in each luminance distribution characteristic of the areas A1', A2' is detected as a centroid position.

Compared with the luminance distribution characteristic of the areas A1', A2' provided in the split luminescent lines SL (311, 31) of the optical image as shown in FIG. 11, the luminance distribution characteristic of the areas A1', A2' provided in the pseudo split luminescent lines SLV (311V, 311V) as shown in FIG. 14 exhibits a pulse-waveform like characteristic that the border between a high luminance area and a low luminance area is well-defined. Thus, calculation of a difference in the centroid positions of the pseudo split luminescent lines SLV (311V, 311V) of the two optical images is carried out more easily and more reliably than calculation of a difference in the centroid positions of the split luminescent lines SL (311, 31) of the two optical images. In other words, the position detection accuracy of the pseudo split luminescent lines SLV (311V, 311V) is higher than the position detection accuracy of the split luminescent lines SL (311, 311) of the optical image.

[Automatic Shoot Operation when Two Split Luminescent Lines are Recognized]

Figure 15A:
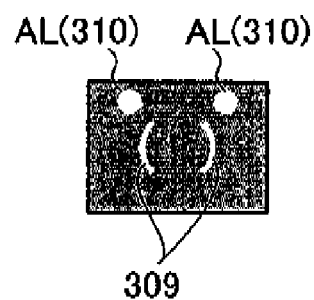
FIG. 15A shows a display example of alignment luminescent spots in the non-mydriasis fundus camera of the first example according to the invention, and also shows a display example when the alignments luminescent spots are not present in ( ) scale.
Figure 15B:
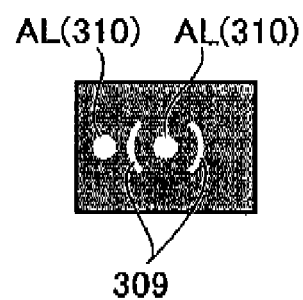
FIG. 15B shows a display example of alignment luminescent spots in the non-mydriasis fundus camera of the first example according to the invention, and also shows a display example when one alignments luminescent spot is present in ( ) scale.
Figure 15C:
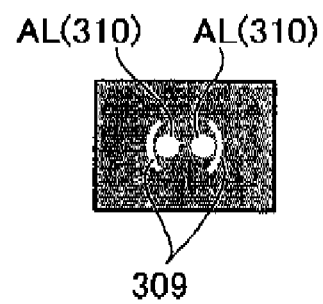
FIG. 15C shows a display example of alignment luminescent spots in the non-mydriasis fundus camera of the first example according to the invention, and also shows a display example when two alignments luminescent spots are present in a spaced manner with each other in ( ) scale.
Figure 15D:
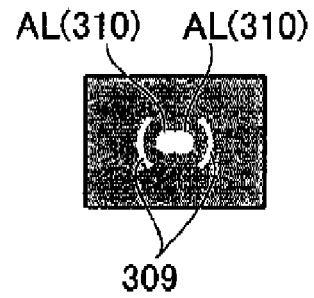
FIG. 15D shows a display example of alignment luminescent spots in the non-mydriasis fundus camera of the first example according to the invention, and also shows a display example when two alignments luminescent spots are present in a close relation with each other in ( ) scale.
Figure 15E:
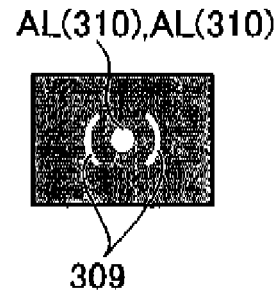
FIG. 15E shows a display example of alignment luminescent spots in the non-mydriasis fundus camera of the first example according to the invention, and also shows a display example when two alignments luminescent spots are coincident and present in ( ) scale.
Figure 16:
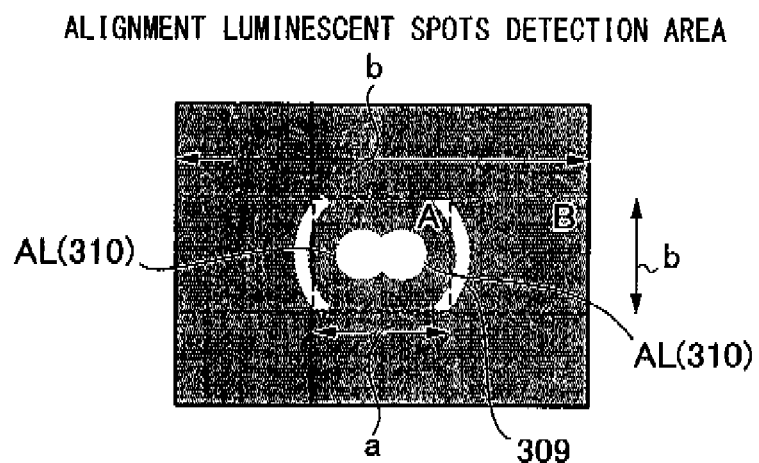
FIG. 16 shows an explanation view of detection areas of alignment luminescent spots during auto alignment operation in the non-mydriasis fundus camera of the first example according to the invention.
Figure 17:
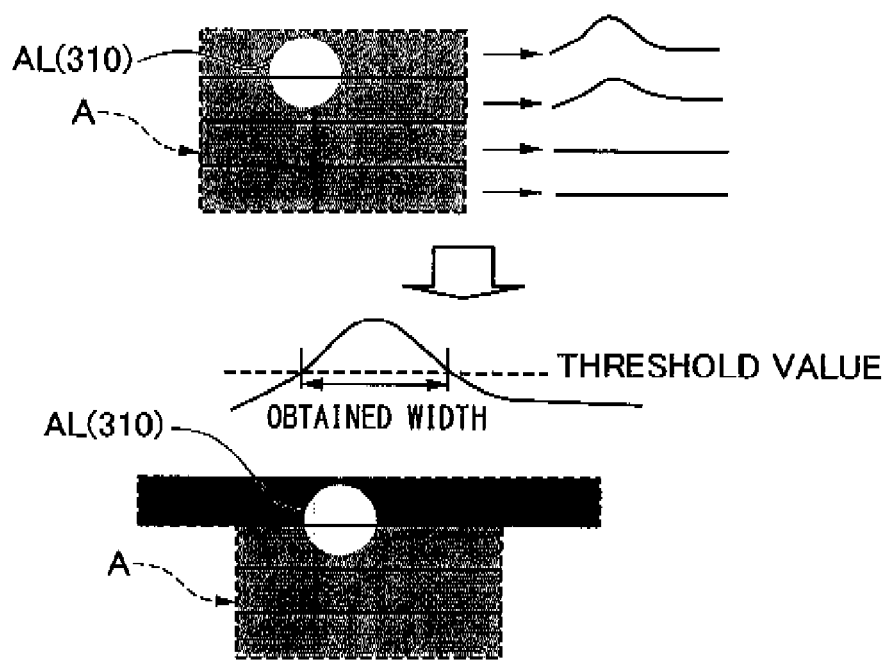
FIG. 17 shows an explanation view of position detection of alignment luminescent spots during auto alignment operation in the non-mydriasis fundus camera of the first example according to the invention.

FIG. 15A to FIG. 15E are classification maps of alignment luminescent spots AL during automatic photographing of an eye fundus when an automatic ON/OFF switch of the non-mydriasis fundus camera of the working example 1 is in an ON state. FIG. 15A shows a state in which the alignment luminescent spot AL are not present in a ( ) scale 309. FIG. 15B shows a state in which one alignment luminescent spot AL is present in the ( ) scale 309. FIG. 15C shows a state in which two alignment luminescent spots are present in a spaced manner with each other in the ( ) scale 309. FIG. 15D shows a state in which two alignment luminescent spots AL (310, 310) are present in a close relation with each other in the ( ) scale 309. FIG. 15E shows a state in which two alignment luminescent spots AL (310, 310) are coincident and present in the scale 309. FIG. 16 is an explanation view of setting of detection areas of alignment luminescent spots in an auto alignment operation during automatic photographing of an eye fundus, with an automatic ON/OFF switch of the non-mydriasis fundus camera of the working example 1 in an ON state. FIG. 17 is an explanation view of detection of a centroid position of an alignment luminescent spot in an auto alignment operation during automatic photographing of an eye fundus, with the automatic ON/OFF switch of the non-mydriasis fundus camera of the working example 1 in an OF state. An automatic shoot operation to be carried out following the autofocus operation described above when two split luminescent lines are recognized will be explained hereinafter.

The automatic shoot operation in an automatic eye fundus photographing mode refers to an operation of automatically emitting flash light to photograph an eye fundus when a focusing condition and an alignment matching condition are met, following an autofocus operation and an auto alignment operation by motor drive control.

In the autofocus operation, when focusing completes either in step S11 of FIG. 6 or step S316 of FIG. 8 and the two split luminescent lines SL (311, 311) are recognized, the flow proceeds to step S16->step S17->step S25->step S26->step S27 in the flow chart of FIG. 7. In step S16, a centroid position of the two alignment luminescent spots AL (310, 310) is detected. In step S17, it is determined whether or not the number of the detected slit luminescent line SL is less than or equal to one. In step S25, according to the determination in step S17 that the number of the split luminescent lines is two (311, 311), a difference between centroid positions of the two alignment luminescent spots AL (310, 310) is calculated, and a motor drive position by the alignment motor 330 is determined. In step S26, the alignment motor 330 is driven at the determined motor drive position and in the determined motor drive direction. In step S27, it is determined whether or not the two alignment luminescent spots AL (310, 310) match in the ( ) scale 309.

Now, a detection of a centroid position of alignment luminescent spots AL in step S16 will be described. As shown in FIG. 15A to FIG. 15E, positions of alignment luminescent spots AL are classified into the following states: a state in which no alignment luminescent spot AL is present in the ( ) scale 309 (FIG. 15A); a state in which one alignment luminescent spot AL (310) is present in the ( ) scale 309 (FIG. 15B); a state in which two alignment luminescent spots AL (310, 310) are present in a spaced manner with each other in the ( ) scale 309 (FIG. 15C); a state in which two alignment luminescent spots AL (310, 310) are present in a close relation with each other in the ( ) scale 309 (FIG. 15D); and a state in which two alignment luminescent spots AL (310, 310) are coincident and present in the scale 309 (FIG. 15E).

As shown in FIG. 16, detection areas of alignment luminescent spots AL are divided into an area A (area surrounded by a horizontal width a and a vertical width c) for detecting alignment luminescent spots AL located in the ( ) scale 309 and an area B (area surrounded by a horizontal width b and a vertical width c) for detecting alignment luminescent spots AL located outside of the ( ) scale 309. Note that the area B is not used except when alignment luminescent spots AL are detected in the area A.

A method of detecting alignment luminescent spots AL is as follows. Firstly, as shown in FIG. 17, the area A is vertically divided into quarters by three horizontal lines. Then, for each divided area, pixel values are accumulated in a vertical direction, and four waveforms representative of the luminance distribution can be obtained. Next, for each waveform, widths of parts, at which a waveform value exceeds a predetermined threshold is calculated. Then, the maximum width of the calculated widths is made a width of the alignment luminescent spot AL (310). In addition, if the maximum width is within the set range, a divided area where waveform having the maximum width is made a position for the alignment luminescent spot AL (310). Then, in the area B (refer to the lower figure of FIG. 17) which corresponds to the divided area where waveform having the maximum width can be obtained, alignment luminescent spots AL are similarly detected. Unless other alignment luminescent spot AL is detected in the area B, the alignment luminescent spot AL is one in the ( ) scale which is considered a state in which the two alignment luminescent spots AL (310, 310) are coincident.

In step S25, based on a positional relationship of the two alignment luminescent spots AL (310, 310) with respect to the ( ) scale 309, a motor drive direction (vertical, right/left, upward/downward) is determined together with a motor drive position. Then, in step S26, an alignment motor 330 is driven in the motor drive position and in the motor drive direction determined in step S25. Then, if it is determined in step 27 that the two alignment luminescent spots AL (310, 310) are not coincide in the ( ) scale ( ), the flow repeats the flow from step S16->step S17->step S25->step S26->step S27 in the flow chart of FIG. 7.

In step S27, if it is determined that the two alignment luminescent spots AL (310, 310) are coincide in the ( ) scale 309, the flow proceeds to step S28 where it is determined whether or not a final check on a state of the split luminescent lines SL ends. In step S28, if it is determined that the final check on the split luminescent lines SL has not ended (the positions of the two split luminescent lines SL (311, 311) are out of the focusing range), the flow returns to step S3, and an autofocus operation is carried out again.

On the one hand, in step S28, if it is determined that the final check on the split luminescent lines SL has ended (the positions of the two split luminescent lines SL (311, 311) are in the focusing range), the flow proceeds to step S29. In step S29, an eye fundus is photographed by the automatic shoot function whereby a shutter of an imaging CCD camera (camera) 6 is automatically released together with light emission of a xenon lamp 17a, and the flow returns to the start.

The automatic shoot operation is automatically carried out to photograph an eye fundus, even when a photographing switch 2c is not pressed, provided that an autofocus operation ends after a match of the two alignment luminescent spots AL (310, 310) is detected and an eye to be examined E does not blink.

In addition, the automatic shoot operation is carried out, if the following conditions are met: 1) accuracy of a focusing state is within ±0.5 D when auto focusing is applied, and 2) an alignment state is within 0.5 mm in a XY direction above an eye to be examined and within 0.3 mm in a Z direction above the eye to be examined.

[Automatic Shoot Operation During Determination of a Small Pupil]

Figure 18A:
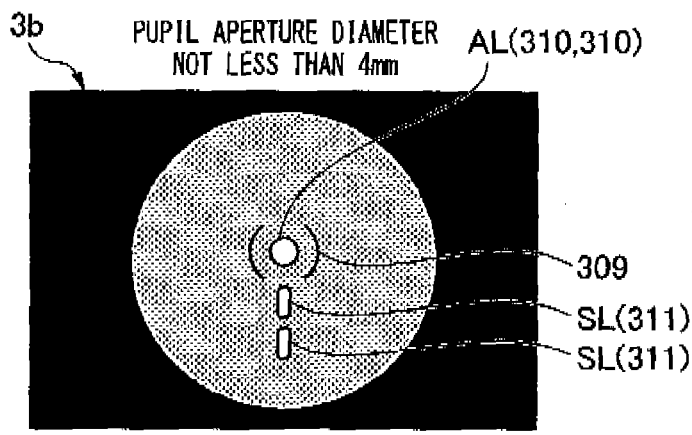
FIG. 18A shows a display example of alignment luminescent spots in the non-mydriasis fundus camera of the first example according to the invention when a pupil diameter of the eye to be examined is not less than 4 mm, two alignment luminescent spots are coincide and two split luminescent lines are displayed.
Figure 19A:
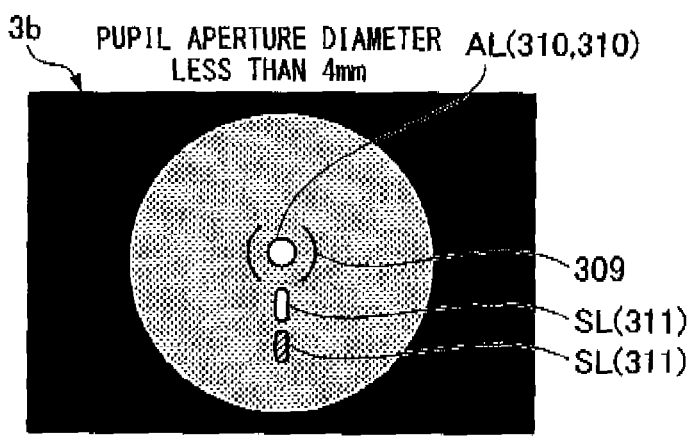
FIG. 19A shows a display example of alignment luminescent spots in the non-mydriasis fundus camera of the first example according to the invention when the pupil diameter of the eye to be examined is less than 4 mm, two alignment luminescent spots are coincide and one split luminescent line is displayed.
Figure 19B:
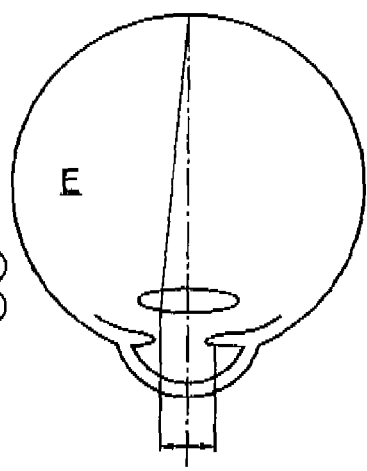
FIG. 19B shows a view illustrative of the relationship between the pupil diameter and an optical path of the split luminescent line in FIG. 19A.
Figure 20:
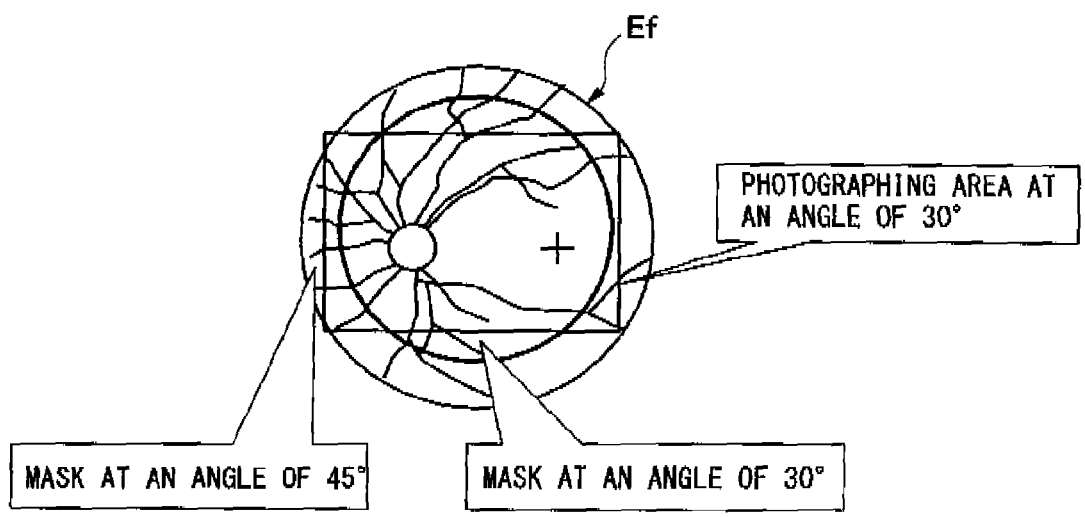
FIG. 20 shows an explanation view of an insertion operation of a small pupil aperture (liquid crystal body aperture) and an electronic mask into the illumination optical system when determining the small diameter pupil in the non-mydriasis fundus camera of the first example according to the invention.

FIG. 18A and FIG. 18D are explanation views of a state in which two split luminescent lines (311, 311) SL appear on a monitor 31 of the non-mydriasis fundus camera of the working example 1. FIG. 18A shows an observation image on the monitor 31 when a pupil diameter of the eye to be examined E is less than or equal to 4 mm and the two alignment luminescent spots AL (310, 310) are coincident. FIG. 18 is a relationship diagram of the pupil diameter in FIG. 18A and an optical path of the split luminescent lines. FIGS. 19A, B are explanation views of a state in which one split luminescent line (311) appears on the monitor 31 of the non-mydriasis fundus camera of the working example 1. FIG. 19A shows an observation image of the monitor 31 when the pupil diameter of the eye to be examined E is within 4 mm and the two alignment luminescent spots AL (310, 310) are coincident. FIG. 19B is a relationship diagram of the pupil diameter of FIG. 19A and the optical path of the split luminescent lines. FIG. 20 is an explanation view of an operation of inserting a small pupil aperture (liquid crystal body aperture) AP and an electronic mask, when the small diameter pupil in the non-mydriasis fundus camera of the working example 1 is determined.

A small pupil photographing operation in an automatic eye fundus photographing mode carries out an operation of automatically inserting a small pupil aperture AP into an illumination optical system when determining a small pupil, in order to achieve the automatic shoot operation that photographs an eye fundus by automatically emitting flash light even if an eye to be examined E has a small pupil.

For example, if an eye to be examined has a small pupil and only one split luminescent line 311 appears on the monitor 31, the flow proceeds from step S17 to step S18->step S19->step S20 in the flow chart of FIG. 7. In step S18, it is determined whether or not a split luminescent line SL recognized in an observation image of the eye fundus is either one or zero. In step S19, following the determination in step S18 that the split luminescent line SL is one, it is determined whether or not the two alignment luminescent spots AL are present in the inner side of a predetermined position, that is, the ( ) scale 309. In step S20, following the determination in step S19 that the two alignment luminescent spots AL are present in the ( ) scale 309, a small pupil aperture (liquid crystal body aperture) AP is inserted into the illumination optical system.

Figure 18B:
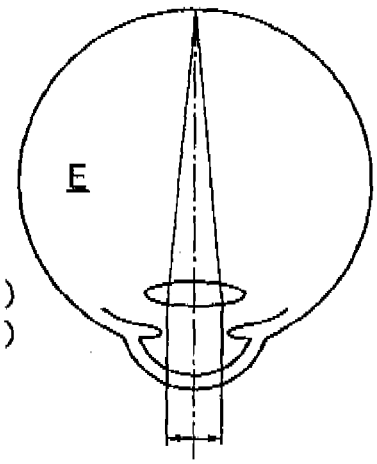
FIG. 18B shows a view illustrative of a relationship between a pupil diameter and an optical path of split luminescent lines in FIG. 18A.

When the two alignment luminescent spots AL (310, 310) are coincident (an eye to be examined E is in an appropriate relationship with the photographing optical system), and a pupil diameter of an eye to be examined E does not have a small pupil (4 mm or larger, for example), the two split luminescent lines SL (311, 311) pass through the pupil of the eye to be examined E as shown in FIG. 18B, and the two split luminescent lines SL (311, 311) appear on the monitor 31 as shown in FIG. 18A.

In contrast, when the two alignment luminescent spots AL (310, 310) are coincident and a pupil diameter of an eye to be examined E has a small pupil (within 4 mm, for example), only one split luminescent line SL (311) passes through the pupil of the eye to be examined E as shown in FIG. 19B, and one split luminescent line SL (311) appears on the monitor 31 as shown in FIG. 19A. Similarly, irrespective of a pupil diameter of an eye to be examined, when two alignment luminescent spots AL (310, 310) are not coincident (the eye to be examined is not in an appropriate relation with the photographing optical system), only one split luminescent line SL (311) passes through the pupil of the eye to be examined E as shown in FIG. 19B, and only one split luminescent line SL (311) appears on the monitor, as shown in FIG. 19A.

Therefore, when only one split luminescent line appears on the monitor 31 and the two alignment luminescent spots AL are coincident, it can be determined that an eye to be examined E has a small pupil.

Thus, when it is determined that the eye to be examined E has a small pupil, use of a light amount determined based on the assumption that the eye to be examined E does not have a small pupil (a pupil diameter is not less than 4 mm) in photographing an eye fundus Ef does not allow a distinct eye fundus image to be photographed, because incident light into the eye fundus Ef is too strong, and this causes flare, etc. Hence, if it is determined that an eye to be examined E has a small pupil, automatic insertion into the illumination optical system of a small pupil aperture (liquid crystal body aperture) AP for controlling a light amount of incident light reaching the eye fundus Ef enables photographing of a distinct eye fundus image.

For example, by inserting the small pupil aperture AP at the angle of view of 30° (high magnification change), it is possible to photograph a small diameter with its pupil diameter up to σ3.3 mm. Then, in the case of the angle of view of 30°, not only a small pupil aperture AP is inserted, and an electronic mask is inserted as a flare preventive measure into the range shown by the thick solid line ring of FIG. 20. In addition, FIG. 20 shows not only the electronic mask with the angle of view of 30°, but also a photographing range for the angle of view of 30° in a rectangle, and a photographing range for the angle of view of 45° in a ring of a thin line.

After the small pupil aperture AP is inserted in the illumination optical system in step S20, the flow proceeds to step S25->step S26->step S27, and even when an eye to be examined E has a small pupil, an eye fundus is photographed by the automatic shoot operation that automatically releases the shutter of the imaging CCD camera (camera) 6 together with light emission of the xenon lamp 17*a*.

[Split Luminescent Line Guiding Action]

For example, when an eye to be examined E has a small pupil and only split luminescent lines SL appear on a monitor 31, an autofocus operation using at least one split luminescent line SL cannot be carried out and an automatic shooting function does not work.

Thus, when an eye to be examined E has a small pupil and the split luminescent lines SL do not appear on the monitor 31, the flow proceeds from step S17 to step S18->step S21 in the flow chart of FIG. 7. In step S21, following the determination in step S18 that the split luminescent lines SL is zero, a small pupil aperture AP is inserted into an illumination optical system, similar to step S20. In fact, since it can be estimated that an pupil diameter of an eye to be examined E has a small pupil (within 4 mm, for example) when the split luminescent lines do not appear on the monitor 31, the small pupil aperture AP is inserted into the illumination optical system similar to when it is determined that the eye to be examined has a small pupil.

In a next step S22, it is determined whether an eye to be photographed is a right eye or a left eye. If it is determined that the eye to be photographed is a left eye, the flow proceeds to step S23, where a guiding instruction instructing an examiner to change an alignment appears on the monitor 31 and the flow proceeds to step S3. Here, display of the guiding instruction is carried out by moving the ( ) scale 309 for a distance corresponding to 0.5 mm on the left eye of the examinee.

In addition, if it is determined that an eye to be photographed is a right eye, the flow proceeds to step S24, where a guiding instruction instructing the examiner to change an alignment appears on the monitor 31, and the flow proceeds to step S3. Here, display of the guiding instruction is carried out by moving the ( ) scale 309 for a distance corresponding to 0.5 mm on the right eye of the examinee.

Therefore, even when an eye to be examined E has a small pupil and the split luminescent line does not appear on the monitor, a guiding instruction instructing an examiner to change the alignment is provided so that as a result of the split luminescent line guiding operation, at least one spirit luminescent line SL appears on the monitor 31. Accordingly, if an eye fundus is photographed in an automatic eye fundus photographing mode and an examiner confirms that the ( ) scale has moved, at least one split luminescent line SL appears on the monitor 31 by the examiner's amending the alignment of the eye to be examined so that the alignment of the eye to be examined is in an appropriate position with respect to the non-mydriasis fundus camera. Therefore, an autofocus operation and automatic shoot operation to be carried out by using one or two split luminescent lines SL can be ensured.

The effects will be described hereinafter. The non-mydriasis fundus camera of the working example 1 according to one embodiment of the invention can achieve the following effects.

(1) The non-mydriasis fundus camera comprises a photographing optical system 20 that photographs an imaging object part (an eye fundus Ef) of an eye to be examined, an illumination optical system 10 that illuminates the eye to be examined, a split target projector system 60 that projects an optical image target or a split target SL for focusing the photographing optical system 20 on the imaging object part Ef of the eye to be examined E, an alignment target projector system 40 that projects the optical image target or an alignment target AL for aligning the photographing optical system 20 with respect to the eye to be examined, an observation optical system 30 that displays optical images of the imaging object part (eye fundus Ef) of the eye to be examined, the split target SL and the alignment target AL on a monitor 31, and a pseudo target display processing unit (board computer 316) that takes an observation video signal output by the observation optical system 30 in, detects at least one of positions of the split target SL and alignment target AL in the observation video signal, and displays a pseudo target on the monitor 31 based on the detected position.

Accordingly, an alignment adjusting operation or a focusing operation can be easily carried out in manual operation, and the alignment adjusting operation or the focusing operation can be surely achieved in automatic operation, regardless of a display condition of a target of an optical image.

(2) The pseudo target display processing unit (board computer 316) detects at least one of positions of the split targets SL and the alignment targets AL in the observation video signal, and overlaps the pseudo target on the detected position and displays it on the monitor 31.

Accordingly, in the case of manual operation, by using the pseudo target, the alignment adjusting operation or the focusing operation can be carried out with the same operating procedure as that of the prior art. In addition, a displayed pseudo target is easier to recognize than the optical image target, and thus visibility of the target will improve. This facilitates the operation of aligning two targets, compared with the case of using the optical image target. Further, in the case of automatic operation, since the pseudo target, which is easier to recognize than the optical image target, is displayed on the monitor 31, performance of position detection of the pseudo target is higher than that of position detection of the optical image target.

(3) A pseudo target display setting unit 218 for setting whether or not the pseudo target is displayed on the monitor 31 is provided, and the pseudo target display processing unit (board computer 316) displays a pseudo target on the basis of setting of the pseudo target display setting unit 218.

Accordingly, it is freely selectable whether or not to display a pseudo target on the monitor, depending on an examiner's skill or a pupil diameter of an eye to be examined E, etc.

(4) The pseudo target display setting unit 218 is configured to be capable of choosing between setting for displaying the pseudo target on the monitor 31, setting for displaying the pseudo target having the same dimension as that of the optical image target on the monitor 31, and setting for displaying the pseudo target having dimension of twice as large as the optical image target on the monitor 31.

Accordingly, when displaying a pseudo target on the monitor 31, it is possible to select size of a pseudo target to be displayed, depending on examiner's level of skill or examiner's preference, etc.

(5) The pseudo target is a pseudo split target SLV that overlaps the optical image target or the split target SL, and the pseudo target display processing unit (board computer 316), when the number of the split target SL detected in the observation video signal is one (311), calculates a position of the other one split target SL (311') on the basis of a preset focusing position, and overlaps a pseudo split target SLV on the position of the split target SL (311) detected in the observation video signal and on the position of the other one calculated split target SL (311') and displays the pseudo split targets SLV on the monitor 31.

Accordingly, when an eye to be examined E has a small pupil, an examiner can easily perform a focusing operation, while looking at two pseudo split targets SLV displayed on the monitor 31. In addition, the two pseudo split targets SLV allow an examiner to achieve focusing by an auto focusing operation in a prompt and reliable manner.

(6) The pseudo target display processing unit (board computer 316), when the pseudo split target SLV is displayed on the monitor 31, changes a color of the pseudo split target SLV upon completion of focusing of the photographing optical system 20.

Accordingly, the color change of the pseudo split targets SLV to be displayed on the monitor makes it possible to confirm completion of focusing.

(7) The photographing optical system 20 comprises a camera (imaging CCD camera 6) having a flash photographing function that photographs an imaging object part Ef of an eye to be examined, and further comprises an automatic photographing control unit (board computer 316) that performs a flash photographing operation of the imaging object part by the camera (imaging CCD camera 6), when an alignment operation of the photographing optical system 20 with the eye to be examined by the alignment target AL and a focusing operation of the photographing optical system 20 on the imaging object part of the eye to be examined by the split target complete, and when precisions of the alignment operation and the focusing operation are within a predetermined range.

Accordingly, irrespective of a display state of split targets SLV of an optical image, focusing completes in a short period of time and a quick automatic flash photographing operation is carried out.

(8) The automatic photographing control unit (board computer 316) determines that an eye to be examined E has a small pupil, when the number of split targets SL detected in an observation video signal is one and two alignment targets AL are positioned within a predetermined range of the observation video signal, and inserts a small pupil aperture into the illumination optical system 10, prior to performing a flash photographing operation.

Accordingly, even when an eye to be examined E has a small pupil, automatic photographing is carried out.

Although the opthalmological imaging apparatus of the invention has been described based upon a working example 1, it is understood that the detailed construction of the invention is not limited to the working example 1 and thus the various design changes and additions may be made in the invention without departing from the spirit, gist and scope of the invention as hereinafter claimed.

Working Example 1

The working example 1, for example, showed the example of using the pseudo target display setting unit 218 as means for switching a pseudo display. However, the pseudo display selection screen may be displayed on the monitor through menu operation, so that a pseudo display may be selected on this selection screen.

The working example 1 has also shown the example of using the two rectangular split luminescent lines SL (311, 311) as split targets and regarding a state in which the two split luminescent lines SL (311, 311) are aligned in a vertical direction as a focusing completed state. However, split targets may take different shapes other than the rectangle. Furthermore, a state in which a plurality of split targets are aligned in a horizontal direction may be regarded as a focused state.

The working example 1 also showed the example of using the two circular alignment luminescent spots AL (310, 310) as an alignment target, and making a state in which the two alignment luminescent spots AL (310, 310) match at the center position of the ( ) scale 309 as a adjustment completed state. However, an alignment target may take different shapes other than the circle. Furthermore, a state in which a plurality of alignment targets match at predetermined positions of a scale indication having a different shape other than the ( ) scale 309 an alignment adjustment completed state.

The working example 1 also showed the example of carrying out the autofocus operation control first and then the auto alignment operation control. However, the auto alignment operation control may precede the autofocus operation control. In addition, the auto alignment operation control and the autofocus operation control may take place simultaneously.

Furthermore, the working example 1 showed the example of pseudo displaying only the split target or the split luminescent lines SL. However, only the alignment target or the alignment luminescent spots AL may be pseudo displayed, or both the split luminescent lines SL and the alignment luminescent spots AL may be pseudo displayed. In short, as far as it is the example of pseudo displaying at least one of the split target or the alignment target, the invention can contain it.

Although the working example 1 shows the example of application of the invention to the non-mydriasis fundus camera, one example of ophthalmic devices, the invention may also be applied to any other ophthalmic devices that need a focusing operation and an alignment adjusting operation. In short, the invention can be applied to any ophthalmic device as far as the ophthalmic device includes a split target projector system, an alignment target projector system, and an observation optical system.

The invention claimed is:

1. An ophthalmic device comprising:
a photographing optical system configured to photograph an imaging object part of an eye to be examined or an eye fundus;
an illumination optical system configured to illuminate the eye to be examined;
a split target projection optical system configured to project an optical image target or a split target so as to focus the photographing optical system on the imaging object part of the eye to be examined;
an alignment target projection optical system configured to project the optical image target or an alignment target so as to align the photographing optical system with respect to the eye to be examined;
an observation optical system configured to display optical images of the imaging object part of the eye to be examined, the split target and the alignment target on a monitor; and
a pseudo target display processing unit configured to take an observation video signal output by the observation optical system in, detect at least one of positions of the split target and the alignment target in the observation video signal, and display a pseudo target on the monitor based upon the detected position, a size of the pseudo target being the same as a size of the split target or larger than the size of the split target, such that when displayed on the monitor, the pseudo target overlaps the split target.

2. The ophthalmic device according to claim 1,
further including a pseudo target display setting part configured to set whether the pseudo target is displayed on the monitor or not,
wherein the pseudo target display processing unit is configured to display the pseudo target based upon a setting of the pseudo target display setting part.

3. The ophthalmic device according to claim 2,
wherein the pseudo target display setting part is configured to select between a setting for displaying the pseudo target on the monitor, a setting for displaying the pseudo target of the same dimension as that of the optical image target on the monitor, and a setting for displaying the pseudo target of a double dimension as that of the optical image target on the monitor.

4. An ophthalmic device comprising:
a photographing optical system configured to photograph an imaging object part of an eye to be examined or an eye fundus;
an illumination optical system configured to illuminate the eye to be examined;
a split target projection optical system configured to project an optical image target or a split target so as to focus the photographing optical system on the imaging object part of the eye to be examined;
an alignment target projection optical system configured to project the optical image target or an alignment target so as to align the photographing optical system with respect to the eye to be examined;
an observation optical system configured to display optical images of the imaging object part of the eye to be examined, the split target and the alignment target on a monitor; and
a pseudo target display processing unit configured to take an observation video signal output by the observation optical system in, detect at least one of positions of the split target and the alignment target in the observation video signal, and display a pseudo target on the monitor based upon the detected position,
wherein the pseudo target is a pseudo split target that overlaps the optical image target or the split target when displayed on the monitor,
and, when the number of the split target detected in the observation video signal is one, the pseudo target display processing unit calculates another split target based upon a predetermined set focusing position, and displays, on the monitor by overlapping the pseudo target, both positions of the split target detected in the observation video signal and the another of the calculated split target.

5. The ophthalmic device according to claim 4,
wherein, when the pseudo split target is displayed on the monitor, the pseudo target display processing unit changes a colour of the pseudo split target upon a completion of focusing of the observation optical system.

6. The ophthalmic device according to claim 5,
wherein the photographing optical system comprises a camera having a flash photographing device configured to photograph the imaging object part of the eye to be examined, and
wherein the ophthalmic device further comprises an automatic photographing control unit configured to perform a flash photographing operation of the imaging object part by the camera, when an alignment operation of the imaging optical system with the eye to be examined by the alignment target and a focusing operation of the imaging optical system with the imaging object part of the eye to be examined by the split target as well as the precisions of the alignment operation and the focusing operation are within a predetermined range.

7. The ophthalmic device according to claim 6,
wherein the automatic photographing control unit is configured to determine whether the eye to be examined is a small pupil, when the number of the split target detected in the observation video signal is one and two alignment targets are positioned within a predetermined range, and insert a small pupil aperture into the illumination optical system, prior to performing the flash photographing operation.

8. The ophthalmic device according to claim 1, wherein the size of the pseudo target is larger than the size of the split target.

* * * * *